US012048647B2

(12) United States Patent
Ivri et al.

(10) Patent No.: US 12,048,647 B2
(45) Date of Patent: Jul. 30, 2024

(54) PIEZOELECTRIC DISPENSER WITH REPLACEABLE AMPOULE

(71) Applicant: Bausch + Lomb Ireland Limited, Dublin (IE)

(72) Inventors: Yehuda Ivri, Newport Coast, CA (US); Mark S. Blumenkranz, Portola Valley, CA (US); Daniel V. Palanker, Sunnyvale, CA (US)

(73) Assignee: Bausch + Lomb Ireland Limited, Dublin (IE)

( * ) Notice: Subject to any disclaimer, the term of this patent is extended or adjusted under 35 U.S.C. 154(b) by 599 days.

(21) Appl. No.: 17/147,196

(22) Filed: Jan. 12, 2021

(65) Prior Publication Data

US 2021/0128350 A1    May 6, 2021

Related U.S. Application Data

(63) Continuation of application No. 15/874,377, filed on Jan. 18, 2018, now Pat. No. 10,888,454.
(Continued)

(51) Int. Cl.
*A61F 9/00* (2006.01)
*B05B 1/08* (2006.01)
(Continued)

(52) U.S. Cl.
CPC ............ *A61F 9/0008* (2013.01); *B05B 1/086* (2013.01); *B05B 9/0838* (2013.01); *B65D 1/095* (2013.01)

(58) Field of Classification Search
CPC ..... A61F 9/0008; B05B 1/086; B05B 9/0838; B65D 1/095
See application file for complete search history.

(56) References Cited

U.S. PATENT DOCUMENTS

| 3,640,274 A | 2/1972 | Costello |
| 3,779,245 A | 12/1973 | Windsor |
(Continued)

FOREIGN PATENT DOCUMENTS

| CN | 103118642 A | 5/2013 |
| CN | 104146816 A | 11/2014 |
(Continued)

OTHER PUBLICATIONS

Abidi et al., "Lifilegrast: A Novel Drug for Treatment of Dry Eye Disease", Journal of Pharmacology and Pharmacotherapy, 2016, vol. 7, pp. 194-198.
(Continued)

*Primary Examiner* — Jessica Arble
(74) *Attorney, Agent, or Firm* — Perilla Knox & Hildebrandt; Stephanie L. Davy-Jow

(57) ABSTRACT

Fluid delivery devices and methods are described, where the device may comprise a piezoelectric actuator operatively coupled to an ampoule with fluid, under a preloading force. The ampoule may comprise a thin-walled thermoplastic package which includes one or more apertures positioned on the wall of the ampoule. The piezoelectric actuator may be configured to clamp at least partially around the circumference of the ampoule and apply oscillations to its wall. The oscillations, typically in ultrasonic frequency, produce cycles of acoustic pressure in the fluid, leading to ejection of the fluid droplets or streams from the apertures.

17 Claims, 18 Drawing Sheets

Related U.S. Application Data

Figures 1A, 1B:
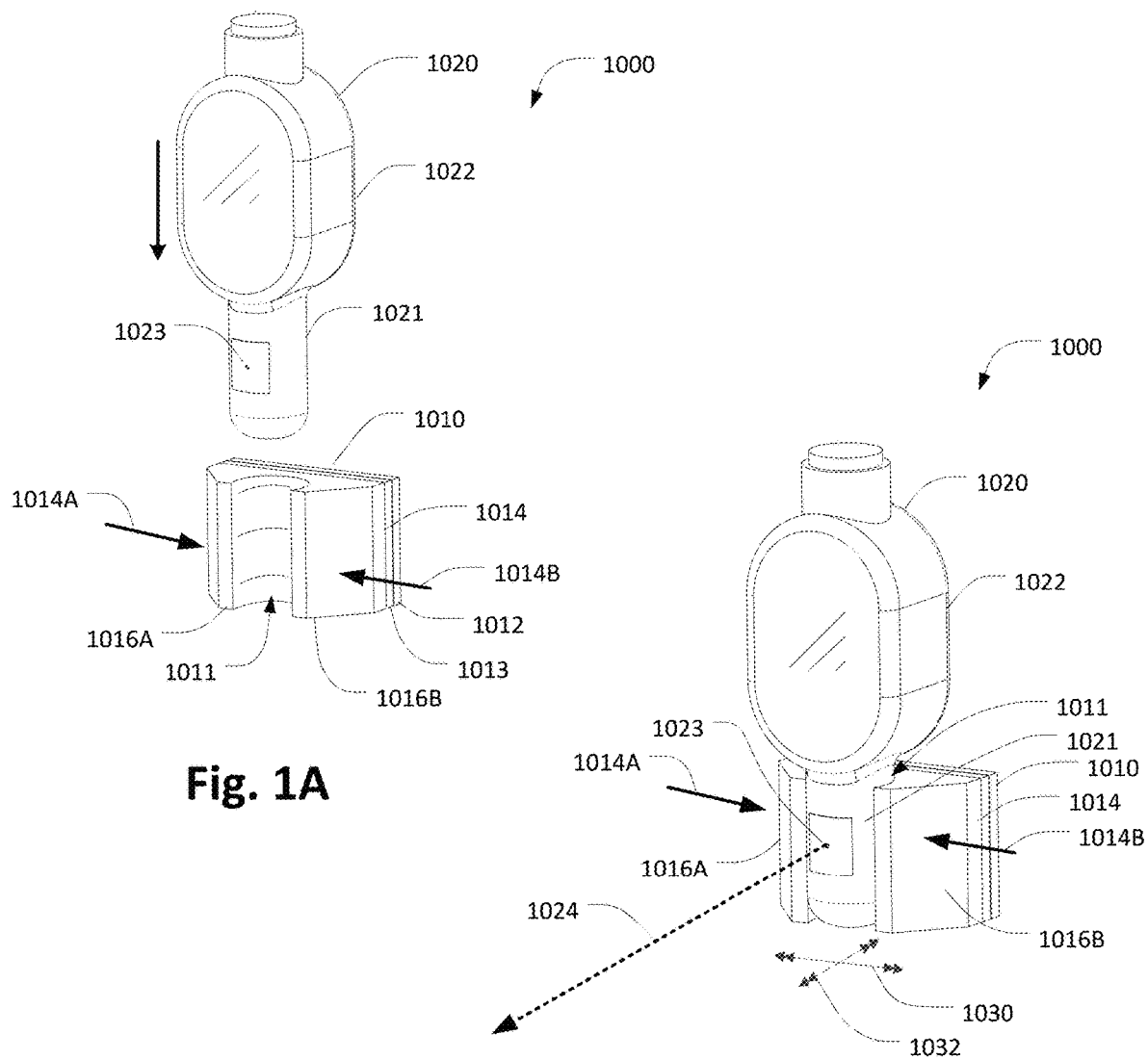

(60) Provisional application No. 62/534,083, filed on Jul. 18, 2017, provisional application No. 62/523,071, filed on Jun. 21, 2017, provisional application No. 62/520,270, filed on Jun. 15, 2017, provisional application No. 62/492,624, filed on May 1, 2017, provisional application No. 62/448,791, filed on Jan. 20, 2017.

(51) Int. Cl.
*B05B 9/08* (2006.01)
*B65D 1/09* (2006.01)

(56) References Cited

U.S. PATENT DOCUMENTS

| | | |
|---|---|---|
| 3,812,854 A | 5/1974 | Michaels et al. |
| 3,861,386 A | 1/1975 | Harris |
| 3,934,585 A | 1/1976 | Maurice |
| 3,970,250 A | 7/1976 | Drews |
| 3,976,072 A | 8/1976 | Walker |
| 4,159,803 A | 7/1979 | Cameto et al. |
| 4,300,546 A | 11/1981 | Kruber |
| 4,334,531 A | 6/1982 | Reichl et al. |
| 4,338,576 A | 7/1982 | Takahashi et al. |
| 4,344,744 A | 8/1982 | Schuster et al. |
| 4,352,459 A | 10/1982 | Berger et al. |
| 4,465,234 A | 8/1984 | Maehara et al. |
| 4,632,311 A | 12/1986 | Nakane et al. |
| 4,655,393 A | 4/1987 | Berger |
| 4,793,339 A | 12/1988 | Matsumoto et al. |
| 4,850,534 A | 7/1989 | Takahashi et al. |
| 4,882,150 A | 11/1989 | Kaufman |
| 4,952,581 A | 8/1990 | Bito |
| 4,961,345 A | 10/1990 | Tsuruoka et al. |
| 4,976,259 A | 12/1990 | Higson |
| 4,981,625 A | 1/1991 | Rhim et al. |
| 5,025,957 A | 6/1991 | Ranalletta |
| 5,171,306 A | 12/1992 | Vo |
| 5,232,363 A | 8/1993 | Meller |
| 5,368,582 A | 11/1994 | Bertera |
| 5,370,317 A | 12/1994 | Weston |
| 5,487,378 A | 1/1996 | Robertson et al. |
| 5,549,249 A | 8/1996 | Foster |
| 5,624,057 A | 4/1997 | Lifshey |
| 5,627,611 A | 5/1997 | Scheiner |
| 5,630,793 A | 5/1997 | Rowe |
| 5,657,926 A | 8/1997 | Toda |
| 5,692,651 A | 12/1997 | Fuchs |
| 5,811,443 A | 9/1998 | DeSantis, Jr. |
| 5,828,394 A | 10/1998 | Khuri-Yakub et al. |
| 5,938,117 A | 8/1999 | Ivri |
| 5,958,342 A | 9/1999 | Gamble |
| 5,960,224 A | 9/1999 | Sanada et al. |
| 6,024,717 A | 2/2000 | Ball |
| 6,062,212 A | 5/2000 | Davison et al. |
| 6,065,623 A | 5/2000 | Hierzer |
| 6,095,376 A | 8/2000 | Hennemann |
| 6,196,218 B1 | 3/2001 | Voges |
| 6,232,129 B1 | 5/2001 | Wiktor |
| 6,273,092 B1 | 8/2001 | Nolan |
| 6,302,101 B1 | 10/2001 | Py |
| 6,467,476 B1 | 10/2002 | Ivri et al. |
| RE38,077 E | 4/2003 | Cohen et al. |
| 6,543,442 B2 | 4/2003 | Gonda |
| 6,629,646 B1 | 10/2003 | Ivri |
| 6,730,066 B1 | 5/2004 | Bennwik et al. |
| 6,758,837 B2 | 7/2004 | Péclat et al. |
| 6,869,275 B2 | 3/2005 | Dante et al. |
| 7,066,398 B2 | 6/2006 | Borland et al. |
| 7,105,357 B1 | 9/2006 | Kalkum |
| 7,201,732 B2 | 4/2007 | Anderson et al. |
| 7,314,938 B2 | 1/2008 | Shen |
| 7,571,722 B2 | 8/2009 | Wuttke |
| 7,745,460 B2 | 6/2010 | Shen |
| 7,790,743 B2 | 9/2010 | Shen |
| 7,874,467 B2 | 1/2011 | Pardes |
| 7,883,031 B2 | 2/2011 | Collins, Jr. et al. |
| 7,928,122 B2 | 4/2011 | Shen |
| 8,012,136 B2 | 9/2011 | Collins, Jr. et al. |
| 8,048,047 B2 | 11/2011 | Domash |
| 8,056,766 B2 | 11/2011 | Grevin |
| 8,128,606 B2 | 3/2012 | Anderson et al. |
| 8,133,210 B2 | 3/2012 | Al-Abdulla et al. |
| 8,144,399 B2 | 3/2012 | Steenblik |
| 8,168,655 B2 | 5/2012 | Gadek |
| 8,273,307 B2 | 9/2012 | Eickhoff et al. |
| 8,367,701 B2 | 2/2013 | Burnier |
| 8,398,001 B2 | 3/2013 | Borland et al. |
| 8,435,544 B2 | 5/2013 | Mitra et al. |
| 8,544,462 B2 | 10/2013 | Papania |
| 8,545,463 B2 | 10/2013 | Collins, Jr. et al. |
| 8,592,450 B2 | 11/2013 | Gadek |
| 8,629,111 B2 | 1/2014 | Acheampong |
| 8,633,162 B2 | 1/2014 | Acheampong |
| 8,642,556 B2 | 2/2014 | Acheampong |
| 8,648,048 B2 | 2/2014 | Acheampong |
| 8,684,980 B2 * | 4/2014 | Hunter ............... B05B 17/0646 604/296 |
| 8,685,930 B2 | 4/2014 | Acheampong |
| 8,722,728 B2 | 5/2014 | Wong et al. |
| 8,733,935 B2 | 5/2014 | Ballou, Jr. et al. |
| 8,863,998 B2 | 10/2014 | Painchaud |
| 8,927,574 B2 | 1/2015 | Burnier |
| 8,927,921 B1 | 1/2015 | Nelms |
| 8,936,021 B2 | 1/2015 | Collins, Jr. |
| 9,039,666 B2 | 5/2015 | Voss et al. |
| 9,068,566 B2 | 6/2015 | Ivri |
| 9,085,553 B2 | 7/2015 | Zeller |
| 9,087,145 B2 | 7/2015 | Ballou, Jr. et al. |
| 9,186,690 B2 | 11/2015 | Scanlon et al. |
| 9,216,174 B2 | 12/2015 | Shen |
| 9,238,532 B2 | 1/2016 | Decock |
| 9,248,191 B2 | 2/2016 | Acheampong |
| 9,353,088 B2 | 5/2016 | Burnier |
| 9,447,077 B2 | 9/2016 | Burnier |
| 9,597,230 B2 | 3/2017 | Haffner et al. |
| 9,676,525 B2 | 6/2017 | Greiner-Perth |
| 9,700,686 B2 | 7/2017 | Gavini et al. |
| 9,801,757 B2 | 10/2017 | Voss et al. |
| 9,808,825 B2 | 11/2017 | Aguilar |
| 9,867,933 B2 | 1/2018 | Pardes |
| 9,890,141 B2 | 2/2018 | Burnier |
| 10,073,949 B2 | 9/2018 | Ballou, Jr. et al. |
| 10,105,720 B2 | 10/2018 | Decock |
| 10,124,000 B2 | 11/2018 | Shen |
| 10,154,923 B2 | 12/2018 | Hunter et al. |
| 10,174,017 B2 | 1/2019 | deLong et al. |
| 10,314,740 B2 | 6/2019 | Kraft |
| 10,624,781 B2 | 4/2020 | Ivri |
| 11,278,448 B2 | 3/2022 | Palanker |
| 2001/0035184 A1 | 11/2001 | Schuler et al. |
| 2001/0036424 A1 | 11/2001 | Takahashi |
| 2001/0036449 A1 | 11/2001 | Garst |
| 2002/0078947 A1 | 6/2002 | Gumaste |
| 2002/0124843 A1 | 9/2002 | Skiba et al. |
| 2002/0158196 A1 | 10/2002 | Berggren et al. |
| 2002/0161344 A1 | 10/2002 | Peclat et al. |
| 2002/0185125 A1 | 12/2002 | Klimowicz |
| 2002/0190079 A1 | 12/2002 | Hamamoto |
| 2003/0052573 A1 | 3/2003 | Wischnewskiy |
| 2003/0065294 A1 | 4/2003 | Pickup |
| 2003/0071071 A1 | 4/2003 | Garcia |
| 2003/0140921 A1 | 7/2003 | Smith et al. |
| 2004/0039355 A1 | 2/2004 | Gonzalez et al. |
| 2004/0050861 A1 | 3/2004 | Lisec |
| 2004/0138630 A1 | 7/2004 | Al-Abdulla et al. |
| 2004/0163645 A1 | 8/2004 | Connelly |
| 2004/0173642 A1 | 9/2004 | Clifford |
| 2004/0204674 A1 | 10/2004 | Anderson et al. |
| 2004/0215157 A1 | 10/2004 | Peclat et al. |
| 2004/0256487 A1 | 12/2004 | Collins, Jr. et al. |
| 2004/0263567 A1 | 12/2004 | Hess et al. |
| 2005/0001981 A1 | 1/2005 | Anderson |

(56) References Cited

U.S. PATENT DOCUMENTS

| | | |
|---|---|---|
| 2005/0006417 A1 | 1/2005 | Nicol et al. |
| 2005/0107832 A1 | 5/2005 | Bernabei |
| 2005/0172962 A1 | 8/2005 | Gumaste et al. |
| 2005/0207917 A1 | 9/2005 | Koerner et al. |
| 2005/0240162 A1 | 10/2005 | Chen et al. |
| 2005/0261641 A1 | 11/2005 | Warchol et al. |
| 2006/0065677 A1 | 3/2006 | Py |
| 2006/0069358 A1 | 3/2006 | Gerondale |
| 2006/0147313 A1 | 7/2006 | Zengerle et al. |
| 2006/0210604 A1 | 9/2006 | Dadey et al. |
| 2007/0051362 A1 | 3/2007 | Sullivan |
| 2007/0088267 A1 | 4/2007 | Shekalim |
| 2007/0088268 A1 | 4/2007 | Edwards |
| 2007/0102455 A1 | 5/2007 | Stark |
| 2007/0119969 A1 | 5/2007 | Collins, Jr. et al. |
| 2007/0195151 A1 | 8/2007 | Anderson |
| 2007/0268340 A1 | 11/2007 | Dacquay |
| 2007/0295332 A1 | 12/2007 | Ziegler et al. |
| 2008/0039807 A1 | 2/2008 | Pine |
| 2008/0202514 A1 | 8/2008 | Kriksunov et al. |
| 2008/0214940 A1 | 9/2008 | Benaron et al. |
| 2008/0233053 A1 | 9/2008 | Gross et al. |
| 2008/0247264 A1 | 10/2008 | Gabl et al. |
| 2008/0257911 A1 | 10/2008 | Choi |
| 2009/0060793 A1 | 3/2009 | Eickhoff et al. |
| 2009/0114742 A1 | 5/2009 | Collins, Jr. |
| 2009/0134235 A1 | 5/2009 | Ivri |
| 2009/0182291 A1 | 7/2009 | Eilat |
| 2009/0192443 A1 | 7/2009 | Collins, Jr. |
| 2009/0212127 A1 | 8/2009 | Reynolds et al. |
| 2009/0212133 A1 | 8/2009 | Collins, Jr. |
| 2009/0223513 A1 | 9/2009 | Papania et al. |
| 2010/0001090 A1 | 1/2010 | Neergaard |
| 2010/0005903 A1 | 1/2010 | Beavis |
| 2010/0013352 A1 | 1/2010 | Pletner et al. |
| 2010/0044460 A1 | 2/2010 | Sauzade |
| 2010/0072301 A1 | 3/2010 | Cater |
| 2010/0072302 A1 | 3/2010 | Cater |
| 2010/0076388 A1 | 3/2010 | Cater |
| 2010/0147899 A1 | 6/2010 | Nardi |
| 2010/0186738 A1 | 7/2010 | Kobayashi et al. |
| 2010/0222752 A1 | 9/2010 | Collins, Jr. et al. |
| 2010/0236545 A1 | 9/2010 | Kern |
| 2010/0295420 A1 | 11/2010 | Wierach |
| 2010/0326431 A1 | 12/2010 | Yu |
| 2011/0074247 A1 | 3/2011 | Hohlfeld et al. |
| 2011/0102735 A1 | 5/2011 | Gupta |
| 2011/0106025 A1 | 5/2011 | Hall et al. |
| 2011/0146670 A1 | 6/2011 | Gallem et al. |
| 2011/0284579 A1 | 11/2011 | Pardes et al. |
| 2011/0293452 A1 | 12/2011 | Kim |
| 2011/0305425 A1 | 12/2011 | Fabrykowski et al. |
| 2012/0017898 A1 | 1/2012 | Moller |
| 2012/0062840 A1 | 3/2012 | Ballou, Jr. et al. |
| 2012/0070467 A1 | 3/2012 | Ballou, Jr. et al. |
| 2012/0143152 A1 | 6/2012 | Hunter et al. |
| 2012/0179122 A1 | 7/2012 | Eilat et al. |
| 2012/0197219 A1 | 8/2012 | Scanlon et al. |
| 2012/0304929 A1 | 12/2012 | Ivri |
| 2013/0002095 A1* | 1/2013 | Van Der Linden .. H10N 30/883 310/340 |
| 2013/0017283 A1 | 1/2013 | Zemel et al. |
| 2013/0025038 A1 | 1/2013 | Frey |
| 2013/0053042 A1 | 2/2013 | Tanikawa et al. |
| 2013/0079733 A1 | 3/2013 | Burt et al. |
| 2013/0118619 A1 | 5/2013 | Loth et al. |
| 2013/0140225 A1 | 6/2013 | Decock |
| 2013/0150812 A1 | 6/2013 | Hunter |
| 2013/0152796 A1 | 6/2013 | Pawl |
| 2013/0153677 A1 | 6/2013 | Leen |
| 2013/0164436 A1 | 6/2013 | Yagi et al. |
| 2013/0172830 A1 | 7/2013 | Hunter et al. |
| 2013/0206857 A1* | 8/2013 | Ivri .................... B05B 17/0669 239/4 |
| 2013/0299607 A1 | 11/2013 | Wilkerson et al. |
| 2013/0345672 A1 | 12/2013 | Ferreri et al. |
| 2014/0088524 A1* | 3/2014 | Marx .................... A61F 9/0026 604/298 |
| 2014/0113946 A1 | 4/2014 | Abad |
| 2014/0157956 A1 | 6/2014 | Date |
| 2014/0171490 A1 | 6/2014 | Gross et al. |
| 2014/0187969 A1 | 7/2014 | Hunter et al. |
| 2014/0214024 A1 | 7/2014 | Eichler |
| 2014/0224267 A1 | 8/2014 | Levitz et al. |
| 2014/0242022 A1 | 8/2014 | Vehige et al. |
| 2014/0249491 A1 | 9/2014 | Ballou, Jr. et al. |
| 2014/0257172 A1 | 9/2014 | Yalamanchili |
| 2014/0274910 A1 | 9/2014 | Cumberlidge et al. |
| 2014/0276054 A1 | 9/2014 | Hossack et al. |
| 2014/0285121 A1 | 9/2014 | Balogh et al. |
| 2014/0323931 A1 | 10/2014 | Avni |
| 2014/0336596 A1 | 11/2014 | Wochele |
| 2014/0336618 A1 | 11/2014 | Wilkerson et al. |
| 2015/0018781 A1 | 1/2015 | Rinderknect et al. |
| 2015/0035180 A1 | 2/2015 | Shen |
| 2015/0036219 A1 | 2/2015 | Shen |
| 2015/0040891 A1 | 2/2015 | Avni |
| 2015/0086397 A1 | 3/2015 | Ma |
| 2015/0097050 A1 | 4/2015 | Ciervo |
| 2015/0139973 A1 | 5/2015 | Steinfeld et al. |
| 2015/0144128 A1 | 5/2015 | Hijlkema |
| 2015/0209174 A1 | 7/2015 | Abreu |
| 2015/0209178 A1 | 7/2015 | Blakey |
| 2015/0238689 A1 | 8/2015 | Shimizu |
| 2015/0256730 A1 | 9/2015 | Shen |
| 2015/0276994 A1 | 10/2015 | Shen et al. |
| 2015/0308421 A1 | 10/2015 | Vogt |
| 2015/0328151 A1 | 11/2015 | Ballou, Jr. et al. |
| 2015/0352297 A1 | 12/2015 | Stedman |
| 2016/0107180 A1 | 4/2016 | Decock |
| 2016/0120833 A1 | 5/2016 | Wan et al. |
| 2016/0129467 A1 | 5/2016 | Ciardella |
| 2016/0199225 A1 | 7/2016 | Ivri |
| 2016/0199230 A1 | 7/2016 | Doshi |
| 2016/0213866 A1 | 7/2016 | Tan |
| 2016/0263314 A1 | 9/2016 | Pardes |
| 2016/0296367 A1 | 10/2016 | Ivri |
| 2016/0354559 A1 | 12/2016 | Gavini et al. |
| 2017/0028626 A1 | 2/2017 | Delrot et al. |
| 2017/0136484 A1 | 5/2017 | Wilkerson et al. |
| 2017/0138357 A1 | 5/2017 | Kondo et al. |
| 2017/0151088 A1 | 6/2017 | Ballou, Jr. et al. |
| 2017/0156927 A1 | 6/2017 | Richter et al. |
| 2017/0182510 A1 | 6/2017 | Wilkerson et al. |
| 2017/0187969 A1 | 6/2017 | Kitamori |
| 2017/0274159 A1 | 9/2017 | Gavini et al. |
| 2017/0344714 A1 | 11/2017 | Ballou, Jr. et al. |
| 2018/0085251 A1 | 3/2018 | Hunter et al. |
| 2018/0108275 A1 | 4/2018 | Newberry |
| 2018/0116871 A1 | 5/2018 | Hunter et al. |
| 2018/0207030 A1 | 7/2018 | Ivri et al. |
| 2018/0229247 A1 | 8/2018 | Laidler |
| 2018/0236466 A1 | 8/2018 | Laidler |
| 2018/0297053 A1* | 10/2018 | Buckland ............ B05B 17/0638 |
| 2019/0053945 A1 | 2/2019 | Hunter et al. |
| 2019/0074086 A1 | 3/2019 | Ballou, Jr. et al. |
| 2019/0099071 A1 | 4/2019 | Ehrmann |
| 2019/0314195 A1 | 10/2019 | Ivri |
| 2019/0314196 A1 | 10/2019 | Ivri |
| 2019/0314197 A1 | 10/2019 | Ivri |
| 2019/0314198 A1 | 10/2019 | Ivri |
| 2020/0022416 A1 | 1/2020 | Alarcon |
| 2020/0197218 A1 | 6/2020 | Newell |
| 2020/0197220 A1 | 6/2020 | Ivri |
| 2020/0246182 A1 | 8/2020 | Ivri |
| 2020/0281768 A1 | 9/2020 | Quintana |
| 2020/0315842 A1 | 10/2020 | Palanker |
| 2020/0330267 A1 | 10/2020 | Li |
| 2021/0137732 A1 | 5/2021 | Quintana |
| 2021/0220169 A1 | 7/2021 | Ivri |
| 2021/0322209 A1 | 10/2021 | Ivri |
| 2021/0322210 A1 | 10/2021 | Ivri |
| 2022/0039998 A1 | 2/2022 | Ivri |

(56) References Cited

U.S. PATENT DOCUMENTS

| | | | |
|---|---|---|---|
| 2022/0125631 A1 | 4/2022 | Ianchulev | |
| 2022/0160542 A1 | 5/2022 | Palanker | |
| 2022/0192874 A1 | 6/2022 | Ivri | |

FOREIGN PATENT DOCUMENTS

| | | | |
|---|---|---|---|
| CN | 104582647 A | 4/2015 | |
| CN | 204813955 U | 12/2015 | |
| CN | 105351426 A | 2/2016 | |
| CN | 107530509 A | 1/2018 | |
| EP | 0622035 A1 | 11/1994 | |
| EP | 0622035 B1 | 3/1999 | |
| EP | 1493410 A2 | 1/2005 | |
| JP | H08251948 A | 9/1996 | |
| JP | 3055480 U | 1/1999 | |
| JP | 2007531577 A | 11/2007 | |
| JP | 2013535250 A | 9/2013 | |
| KR | 10-1258025 B1 | 4/2013 | |
| KR | 10-2013-0054352 A | 5/2013 | |
| WO | 1994020875 A3 | 1/1995 | |
| WO | 1996000050 A1 | 1/1996 | |
| WO | 2000005482 A1 | 2/2000 | |
| WO | 2001046134 A1 | 6/2001 | |
| WO | 2002072169 A2 | 9/2002 | |
| WO | 2010078428 A1 | 7/2010 | |
| WO | 2012009706 A1 | 1/2012 | |
| WO | 2013076682 A1 | 5/2013 | |
| WO | 2013090459 A1 | 6/2013 | |
| WO | 2013090468 A1 | 6/2013 | |
| WO | 2013155201 A2 | 10/2013 | |
| WO | 2013158967 A2 | 10/2013 | |
| WO | 2016115050 A1 | 7/2016 | |
| WO | 2016164830 A1 | 10/2016 | |
| WO | WO2016164830 | 10/2016 | |
| WO | 2018136618 A2 | 7/2018 | |
| WO | 2018227190 A1 | 12/2018 | |
| WO | 2019113483 A1 | 6/2019 | |
| WO | 2020010116 A1 | 1/2020 | |

OTHER PUBLICATIONS

Ali et al., "Glaucoma and Dry Eye", Ophthalmology, 2009, vol. 116, p. 1232.
Choi et al., "Generation of Controllable Monodispersed Sprays Using Impulse Jet and Charging Techniques", Review of Scientific Instruments, 1990, vol. 61, pp. 1689-1693.
Jow et al., "Design and Optimization of Printed Spiral Coils for Efficient Transcutaneous Inductive Power Transmission", IEEE Transactions on Biomedical Circuits and Systems, 2007, vol. 1, pp. 193-202.
Kent, Christopher, "Getting Meds onto the Eye, 21st Century Style", Mar. 15, 2013 [online]; [Retrieved on Aug. 27, 2019], Retrieved from the Internet <URL: https://www.reviewofophthalmology.com/article/getting-meds-onto-the-eye-21st-century-style>.
Lallemand et al., "Cyclosporine A Delivery to the Eye: A Comprehensive Review of Academic and Industrial Efforts", European Journal of Pharmaceutics and Biopharmaceutics, 2017, vol. 117, pp. 14-28.
Lindblad et al., "Production of Uniform-Sized Liquid Droplets", Journal of Scientific Instruments, 1965, vol. 42, pp. 635-638.
Lux et al., "A Comparative Bioavailability Study of Three Conventional Eye Drops Versus a Single Lyophilisate", Br. J. Ophthalmol., 2003, vol. 87, pp. 436-440.
Macmillan Online Dictionary, "Stream," n.d. [online]; [Retrieved on Dec. 13, 2018]; Retrieved from the Internet <URL: https://macmillandictionary.com/dictionary/american/stream_ 1#stream_ 9>.
Merriam-Webster, "Clamp," 2019 [online]; [Retrieved on Oct. 25, 2022], Retrieved from the Internet <URL: https://www.merriam-webster.com/dictionary/clamp>.
Murube et al., "Classification of Artificial Tears, I: Composition and Properties", Advanced Experimental Medical Biology, 1998, vol. 438, pp. 693-704.
Murube et al., Classification of Artificial Tears, II: Additives and Commercial Formulas, Advanced Experimental Medical Biology, 1998, vol. 438, pp. 705-715.
Oxford Online Dictionary, "Stream," n.d. [online]; [Retrieved on Dec. 13, 2018]; Retrieved from the Internet <URL: https://en.oxforddictionaries.com/definition/us/stream>.
Vocabulary.com, "Stream," n.d. [online]; [Retrieved on Dec. 13, 2018]; Retrieved from the Internet <URL: https://www.dictionary.com/stream>.
International Search Report and Written Opinion dated Jul. 23, 2018 in corresponding International Patent Application No. PCT/US2018/014211 (23 pages).
Birkhoff et al., "New Devices for Dispensing Ophthalmic Treatments May be the Key to Managing the Life Cycles of Established Products", 2010, Drug Delivery Technology, vol. 10, pp. 16-21.
Brenton, "CRUK/10/30: TRICON8—Sample collection of ovarian cancer tissues and blood for translational research from patients participating in the CR-UK/MRC ICON8 trial", 2015, online abstract.
Denion et al., "A 5-Minute Interval between Two Dilating Eye Drops Increases Their Effect", Jul. 19, 2017, Optometry and Vision Science, vol. 94, pp. 838-844.
Electronic Tutorials, "Linear Solenoid Actuator", 2016 [online]; [Retrieved on Oct. 17, 2022], Retrieved from the Internet [URL: https://www.electronics-tutorials.ws/io/io_6.html].
Elert, Glenn, "Spherical mirrors", The Physics Hypertextbook, 2021 [online]; [Retrieved on Oct. 17, 2022], Retrieved from the Internet [URL: https://physics.info/mirrors/].
Gannon, Megan, "The Best Length for Eyelashes, According to Science", Feb. 24, 2015 [online]; [Retrieved on Oct. 17, 2022], Retrieved from the Internet [URL: https://www.livescience.com/49934-optimal-length-for-eyelashes-discovered.html].
Ianchulev et al., "Pharmacodynamic profile of mydriatic agents delivered by ocular piezo-ejection microdosing compared with conventional eyedropper", 2016, Ther. Deliv., vol. 7, pp. 751-760.
Kompella et al., "ISOPT Clinical Hot Topic Panel Discussion on Ocular Drug Delivery", 2019, J. Ocul. Pharmacol. Ther., vol. 35, pp. 457-465.
Marx et al., "Opthalmic Squeeze Dispenser: Eliminating the Need for Additives in Multidose Preservative-Free Eyecare Formulations", 2017, Drug Development Delivery, vol. 17, pp. 40-44.
Merriam-Webster, "Collimate," 2020 [online]; [Retrieved on Oct. 17, 2022], Retrieved from the Internet [URL: https://www.merriam-webster.com/dictionary/collimated].
Merriam-Webster, "Stream," n.d. [online]; [Retrieved on Dec. 13, 2018], Retrieved from the Internet [URL: https://www.merriam-webster.com/dictionary/stream].
Pronin et al., "Teaching an Old Drug New Tricks: Agonism, Antagonism, and Biased Signaling of Pilocarpine through M3 Muscarinic Acetylcholine Receptor", 2017, Mol. Pharmacol., vol. 92, pp. 601-612.

* cited by examiner

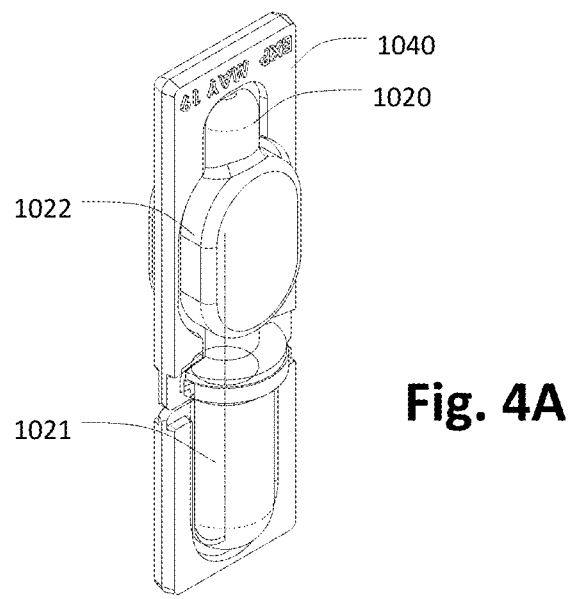
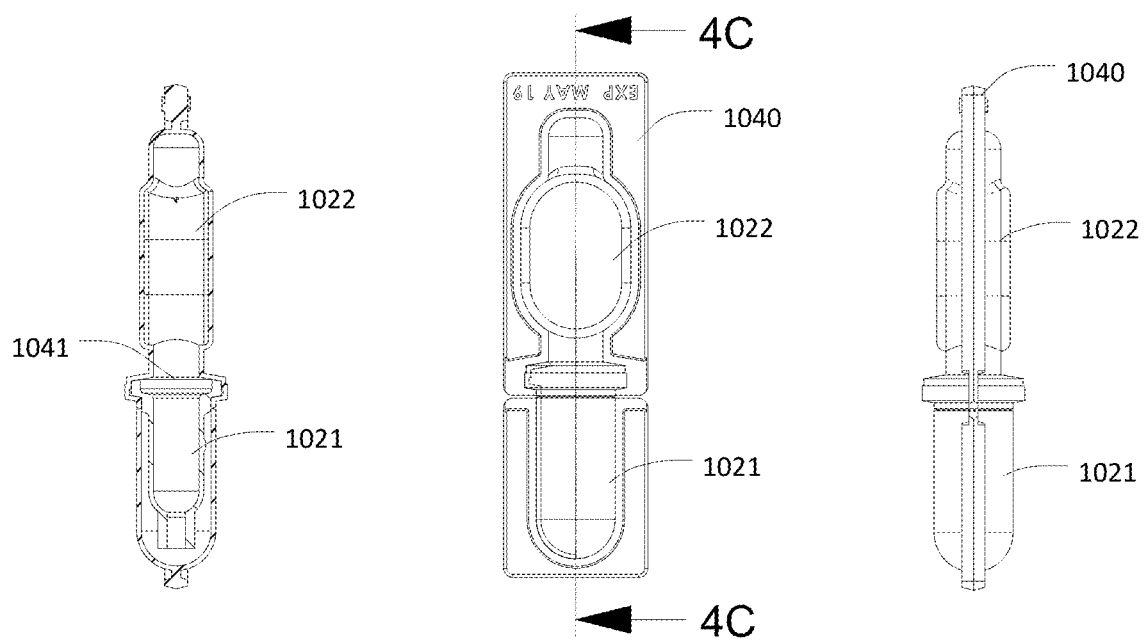
Fig. 4C    Fig. 4B    Fig. 4D

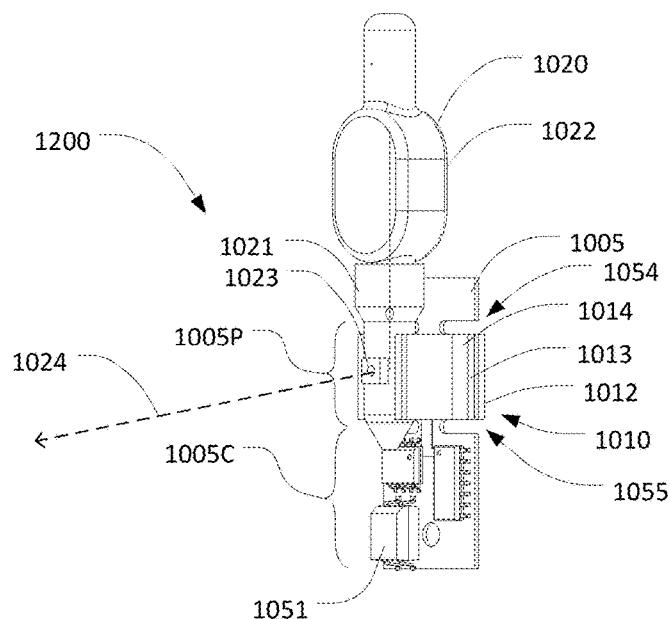
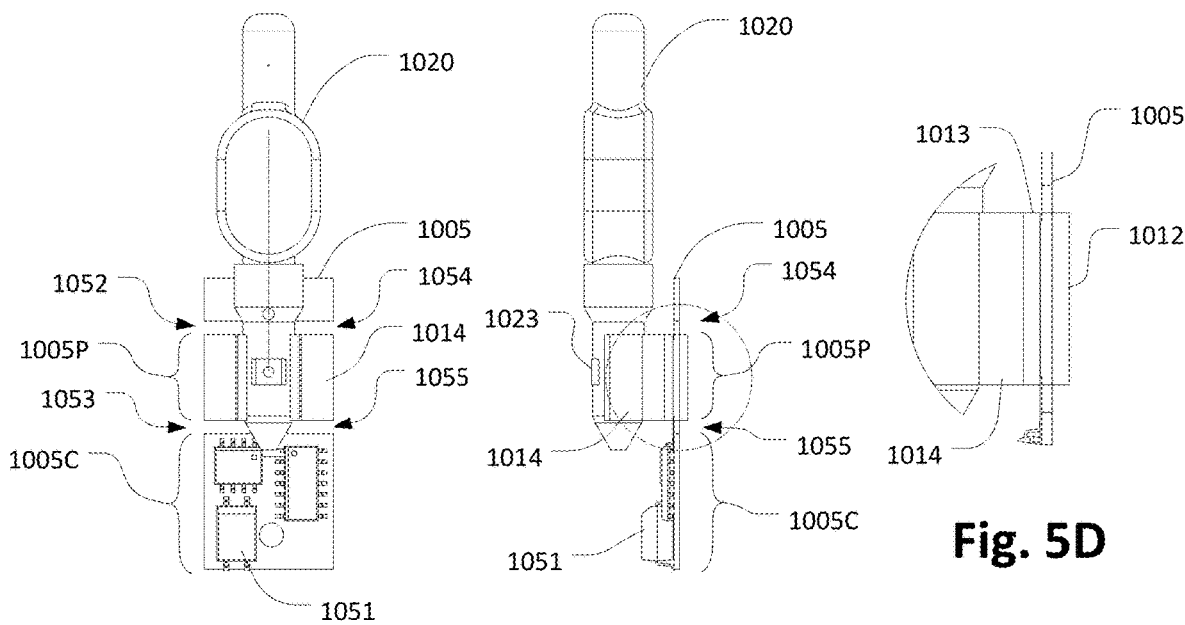
Fig. 5A
Fig. 5B    Fig. 5C    Fig. 5D

PIEZOELECTRIC DISPENSER WITH REPLACEABLE AMPOULE

CROSS-REFERENCE TO RELATED APPLICATIONS

This application is a continuation of U.S. patent application Ser. No. 15/874,377 filed Jan. 18, 2018 and hereby incorporated by reference in its entirety. application Ser. No. 15/874,377 claims the benefit of priority to U.S. Prov. Pat. Apps. 62/448,791 filed Jan. 20, 2017; 62/492,624 filed May 1, 2017; 62/520,270 filed Jun. 15, 2017; 62/523,071 filed Jun. 21, 2017; and 62/534,083 filed Jul. 18, 2017, each of which is incorporated herein by reference in its entirety.

FIELD OF THE INVENTION

The present invention relates to devices for ejecting a fluid stream, specifically but not exclusively, for topical ophthalmic applications.

BACKGROUND OF THE INVENTION

A typical medical eye dropper dispenses single drops that are about 40-50 μL in volume. However, since the human eye can typically retain only 7 μL of fluid on the corneal surface, larger deposited volumes result in overflow and loss of most of the medication from the eye surface. In addition, a large volume of a single drop, such as 30 or 50 μL, causes a blinking reflex, which removes the majority of the fluid from the ocular surface, and also causes discomfort and reflex tearing. These factors together can make self-administration of eye drops unpleasant, which can lead to poor compliance. As examples, droplet generating devices are described in further detail in U.S. Pat. Nos. 5,630,793 and 8,684,980 (each of which is incorporated herein by reference in its entirety) for drug delivery to the eye. These devices generally comprise a piezoelectric actuated droplet generator for delivering small droplets to the eye and further incorporate a piezoelectric fluid ejector to dispense droplets to the surface of the eye. Such ejector mechanisms are integrally coupled to a fluid reservoir which may be periodically refilled by the user. Refilling, however, carries the risk of bacterial contamination and may result in ocular infection. Generally, drug filling or refilling of fluid reservoirs, particularly for ophthalmic use, must be processed in a tightly controlled aseptic environment which is generally not available to the typical user.

Another problem associated with aerosol or jet delivery, as described in the prior art, is the user's ability to accurately direct the aerosol stream to the surface of the eye. Any misalignment of the dispensing device with the eye can result in inaccurate dosing.

The devices and methods described herein for ejecting therapeutic fluids to the cornea or to the conjunctival tissue of the eye advantageously utilize a disposable sterile drug ampoule which may include a dispensing nozzle and where the ampoule can be readily attached to and detached from a piezoelectric transducer thereby eliminating the need for refilling. This mitigates the possibility of bacterial contamination and provides a cost effective approach by reusing the piezoelectric actuator for further operation.

The devices and methods described further provide for delivery of a liquid stream and a mechanism to align the stream to the eye prior to actuation to ensure convenient and precise dosing. In one variation, it has been found that delivery of a single stream surprisingly causes less discomfort to the eye and is therefore more convenient compared to delivery of a mist or a random distribution of small droplets which have the same total volume. Unlike a mist or spray, streams can be precisely oriented to target a specific location on the cornea or the conjunctival tissue of the eye. This characteristic is largely attributed to the aerodynamic behavior of a stream. Specifically, delivery of a mist involves turbulence which causes divergence of the droplets from the target while a stream propagates through the air and reaches the target area more precisely.

SUMMARY OF THE INVENTION

Fluid ejection devices for emitting a fluid to a body region of a subject, e.g., for treatment of ophthalmic diseases, by topical administration are described where a disposable drug or fluid package such as an ampoule may be separate or separable from a piezoelectric actuator. The piezoelectric actuator is configured to oscillate the ampoule thereby generating acoustic pressure in the fluid therein which in turn produces cycles of acoustic pressure in the fluid and ejection of droplets or a stream of fluid from one or more apertures defined along the ampoule. The ampoule drug packaging can be easily attached to or detached from the piezoelectric actuator assembly and the empty drug or fluid packages are disposable, thereby eliminating the need for filling the drug by the user and the risk of bacterial contamination. In one embodiment, only the ampoule is disposable, while in another embodiment, the entire assembly including the piezoelectric actuator and the ampoule are disposable.

The embodiments and features described herein may be utilized in any number of combinations with the various features described in further detail in U.S. patent application Ser. No. 14/992,975 filed Jan. 11, 2016 (U.S. Pat. Pub. 2016/0199225); U.S. patent application Ser. No. 15/094,849 filed Apr. 8, 2016 (U.S. Pub. 2016/0296367), each of which is incorporated herein by reference in its entirety and for any purpose.

The piezoelectric fluid ejection device is configured to dispense the contents of a fluid-filled ampoule directly and eliminates the need to transfer the contents of the ampoule to a secondary dispensing device and the need to sterilize the dispensing device prior to fluid filling. This particularly useful for delivery of ophthalmic solutions to the surface of the eye. The device generally comprises a piezoelectric clamping actuator and separable disposable fluid-filled ampoule which in one variation comprises a thin-walled thermoplastic package which includes a first or proximal section (e.g., a conduit portion) and a second or distal section (e.g., a bulb portion). One or more apertures may be positioned on the wall of the first section of the ampoule.

The piezoelectric clamping actuator may be configured to clamp about the first section while leaving the one or more apertures uncovered to allow for the fluid to be emitted. In one embodiment, the clamping actuator may be configured to clamp at least partially around the circumference of the first section adjacent to the one or more apertures while and simultaneously applying cycles of oscillations in the clamping direction. The oscillations, typically in ultrasonic frequency, produce cycles of acoustic pressure in the fluid contained within the ampoule which forces the ejection of fluid droplets or a stream of fluid from the one or more apertures. The fluid-filled ampoule may be held in a first orientation, e.g., vertically relative to the ground, while fluid droplets or a stream is ejected in a second orientation, e.g., horizontally. In this way, the fluid is continuously fed from the second reservoir section to the first conduit section of the ampoule while fluid droplets or the stream may be ejected horizontally from the one or more apertures. This orientation is particularly useful for delivery to the surface of the eye. Advantageously the fluid may be ejected directly from the ampoule without having to transfer the fluid content to a container in a step that normally requires sterilization of the container.

The ampoule can be easily coupled or decoupled from the piezoelectric clamp actuator so that empty drug or fluid packages may be readily disposed to eliminate the need for filling the drug by the user and the risk of bacterial contamination. The fluid package may be coupled to the clamp by, e.g., a friction or interference fit, and may generally require an insertion force that is less than, e.g., 5 Newton, or less than, e.g., 10 Newton. The amount of insertion force may accordingly be adjusted.

The drug or fluid package is configured to dispense micro-droplets by one or more oscillations exerted by the piezoelectric actuator clamp onto the external surface or the conduit portion of the ampoule drug package. The ampoule can be decoupled from the piezoelectric actuator allowing disposal of used packages while the piezoelectric clamping transducer may be subsequently reused with another ampoule to provide a cost effective approach, e.g., for topical drug delivery to the eye. The ampoule (or at least portions of the ampoule) may be manufactured, e.g., by a blow-fill-seal process, in which the ampoule may be filled and sealed while it is retained in a mold cavity. Such processes are described for example in U.S. Pat. Pub. 2013/0345672 A1; 2012/0017898; and U.S. Pat. No. 5,624,057, each of which is incorporated herein by reference in its entirety and for any purpose. The ampoule itself may be fabricated of, e.g., a thermoplastic polymer such as terephthalate, polyethylene or polypropylene, either high density or low density, etc.

The piezoelectric clamping actuator may be configured as a relatively small module which can be used in a handheld device or, e.g., as an attachment to an eyewear article such as spectacles or sunglasses.

In one embodiment the fluid ejection device may comprise a piezoelectric clamp configured to oscillate at ultrasonic frequency and further includes an ampoule containing a fluid to be dispensed. Ultrasonic oscillations which are generated by the clamp actuator may be transmitted to the conduit portion of the ampoule and produces cycles of acoustic pressure in the fluid thus forcing the ejection of droplets from one or more apertures in the ampoule.

In one embodiment, the piezoelectric transducer includes a clamp having two jaws which are structurally connected to a bending actuator which may generally be comprised of a laminate having two active piezoceramic plates oriented in opposite polarity. Such a bending actuator is generally known as a bimorph actuator which oscillates in a bending mode causing the clamp to cyclically open and close against the conduit of the ampoule.

In another embodiment, the bending actuator may comprise a laminate of two active piezoceramic plates and one passive plate positioned between the two piezoceramic plates. The passive layer may comprise, e.g., a printed circuit board (PCB) made of FR-4 material. The PCB may include a controller having electronic circuitry for driving and controlling the piezoceramic clamp. The piezoceramic plates may be attached to the PCB by a solder reflow process where the electrical connections to the piezoceramic plates may be made via, e.g., one or more copper pads on the PCB.

The controller having the electronic circuitry may be in electrical communication with the bending actuator and may generally comprise circuitry that is configured to generate and transmit one or more electric pulses or waveforms to the piezoelectric actuator. In one embodiment, the circuitry may be comprised of a half-bridge driver which may include a half-bridge driver chip and two MOSFET transistors. The half-bridge driver receives an input signal and transmits a switching output which drives a pair of MOSFET transistors sequentially "on" and "off". In this way, it translates the low voltage input signal to a high power electrical pulse that is capable of driving the piezoelectric actuator. The circuit may further include an inductor which boosts the input voltage to the piezoelectric actuator. The inductance of the inductor and the capacitance of the piezoelectric actuator may be tuned to operate in electrical resonance at the selected frequency. The input signal which is transmitted to the half-bridge driver chip may be generated by a microprocessor or by a signal generator IC (integrated circuit).

In one embodiment of the driver, the transistors and the microprocessor may be fabricated on a single integrated circuit. Such an IC may be attached and encapsulated directly to a PCB utilizing a chip-on-board (COB) packaging process. In the field of microelectronics COB is used to reduce the size of the circuit. The input voltage of the circuit is preferably below, e.g., 5 volts, and more preferably below, e.g., 3 volts, and even more preferably below, e.g., 1.5 volts. The source of energy may be provided by a power supply such as capacitors, batteries, etc. which may be optionally rechargeable. When the circuit is driven sequentially "on" and "off" as described earlier, the fluid stream emits from the one or more apertures as individual droplets. However, when an inductor is added and is tuned to operate at the electrical resonance of the circuit then the electrical output becomes sinusoidal and the fluid emits either as a collimated and continuous stream without individual droplets, or as a collimated, discontinuous stream of individual droplets.

The droplet volume emitted from the device, in one variation, may range generally between, e.g., 100 to 1000 pL, and the size of the aperture may range typically between, e.g., 10 to 100 micron in the case of a discontinuous stream of droplets. In the case of a continuous stream of fluid, the stream diameter may range to be similar to the range of diameters of the apertures of between, e.g., 0.070-0.130 mm, and the total volume will be determined by the duration. Furthermore, various fluids, compositions, and/or therapeutics may be used with the devices and methods described herein for containment within the ampoule and emission through the one or more apertures. For instance, U.S. Pat. Pub. 2012/0070467 (the entirety of which is hereby incorporated by reference herein and for any purpose) describes examples of various ophthalmic compositions and therapeutics which may be used with the devices and methods described herein.

In other embodiments, the dispensing device may include an optical mechanism to align or target the dispensing aperture to the ocular surface or to the area of the conjunctiva prior to actuation. Such alignment assures that the entire dose reaches the surface of the eye. It may include a tubular member with proximal and distal openings where the distal opening may be positioned near a visible light source such as red LED or the like while the proximal opening of the tube is brought into proximity near the eye of the user. The tubular member may be parallel to the droplet projection direction but may be placed by a predetermined offset. Prior to actuation of the dispensing device, the user may align the eye to be treated with the proximal opening of the tube and then manipulate the orientation of the device until the light at the distal end of the tube becomes visible. In this way the device is brought to an alignment with the optical axis of the eye to be treated or the center of the pupil. The dispensing nozzle may be positioned at a predetermined small offset relative to the optical axis of the tube. When the device is actuated, a stream of fluid will reach the targeted surface of the cornea or the conjunctival tissue and will deposit fluid at the above mentioned offset from the optical axis of the eye.

It should be noted that the alignment or targeting method described herein may be used for aligning the nozzle to the eye in any topical delivery system or eye dropper including a squeeze bottle.

The optical tube may have a length of, e.g., 20, 30, or 40 mm while its internal diameter ranges between, e.g., 1 to 5 mm. Optionally, the internal surfaces of the tube may be coated with optically-black non-reflective coating.

A typical volume of, e.g., between 1 and 10 µL, may be delivered to the eye during the time of fixation of the eye on the target, typically under 1 second, and preferably within 250 msec in one variation or within 400-600 msecs in another variation. In one embodiment the dispensing device includes one or more apertures but typically less than, e.g., 20 apertures, and preferably less than, e.g., 10 apertures, and most preferably a single aperture. The apertures are positioned in a predetermined offset relative to the optical axis of the alignment tube. This offset determines where the fluid stream is deposited relative to the optical axis of the eye or relative to the center of the pupil or to the center of the iris. Typically, the offset may be, e.g., 2-20 mm, from the center of the pupil in the vertical or horizontal directions, or in both vertical and horizontal directions.

In other variations where multiple apertures are utilized for dispensing, each of the apertures may be configured to preserve the uniqueness of an individual stream rather than forming a mist. Factors such as aperture size and spacing between the apertures may be adjusted accordingly to maintain the formation of the individual streams of fluid and to minimize or inhibit the merging or conflation of the individual fluid streams. For instance, apertures having a relatively larger size, e.g., 80-100 microns, may allow for both relatively shorter pulse durations to deliver an equivalent volume of fluid. Furthermore, apertures having such a size may also allow for the use of fluids having a relatively higher viscosity such as artificial tears which are generally comprised of methylcellulose or carboxy-methylcellulose, hyaluronic acid derivatives or other hydrogels which would otherwise block or clog smaller sized apertures in the range of, e.g., 10-12 microns.

The fluid or fluids which may be used with the dispensing device may vary to include any number of agents depending upon, e.g., the treatment, the region of the body where the fluid is applied, etc. Examples of various fluids or agents which can be used may include (but are not limited to), e.g., anti-infectives (including but not limited to antibiotics, antivirals, etc.); anti-inflammatories (including but not limited to steroids and non-steroidal anti-inflammatory drugs (NSAIDS), etc.); anti-allergy (including but not limited to anti-histamines and mast cell stabilizers, etc.); anti-fungals; vasoconstrictors; mydriatic (pupil dilating) agents; miotic agents (pupil constricting agents); biologics (e.g. proteins, engineered proteins, etc.); small molecules; anesthetics; analgesics; intraocular pressure lowering agents (including but not limited to prostaglandin analogs, ROK inhibitors, beta blockers, carbonic anhydrase inhibitors, and alpha agonists, etc.); lubricants (including but not limited to saline, polymer solutions, proteoglycans, glycosaminoglycans, carbohydrates, etc.); iodine derivatives; etc. and/or various combinations thereof. Additional drugs and agents which may be utilized with the devices described may include any number of the agents disclosed in further detail in U.S. Pub. 2017/0344714 and U.S. Pat. No. 9,087,145 which are each incorporated herein by reference and for any purpose.

In one variation of the dispensing apparatus, the apparatus may generally comprise an ampoule containing a liquid to be dispensed and having a first portion and a second portion, wherein the first portion defines one or more apertures, and a piezoelectric assembly which is configured to secure the first portion and impart a primary oscillation to the first portion along a first direction such that a secondary oscillation is induced in the first portion along a second direction which is perpendicular to the first direction. The primary oscillation and secondary oscillation may be co-planar with one another, and the one or more apertures may be aligned along the second direction such that the secondary oscillation dispenses a stream of the liquid through the one or more apertures.

In another variation, the fluid dispensing apparatus may generally comprise a fluid reservoir having a proximal section and a distal section, wherein a side surface of the proximal section defines one or more apertures. The apparatus may also include a clamp member which defines a receiving channel sized to retain the proximal section of the fluid reservoir and a piezoelectric actuator in vibrational communication with the clamp member, wherein actuation of the piezoelectric actuator deforms the clamp member to impart a primary oscillation to the proximal section along a first direction such that a secondary oscillation is induced in the proximal section along a second direction which is perpendicular to the first direction. The primary oscillation and secondary oscillation may be co-planar with one another, and the one or more apertures may be aligned along the second direction such that the secondary oscillation induced within the proximal section is sufficient to eject a fluid through the one or more apertures.

In another variation for dispensing a fluid, the method may generally comprise providing a piezoelectric assembly configured for removable engagement with a fluid reservoir, imparting a primary oscillation along a first direction to a proximal section of the fluid reservoir such that a secondary oscillation is induced in the proximal section along a second direction which is perpendicular to the first direction, wherein the primary oscillation and second oscillation are co-planar with one another, and ejecting a fluid from one or more apertures defined along a side surface of the proximal section, wherein the one or more apertures are aligned along the second direction.

In another embodiment, the fluid ejection device may generally comprise at least one piezoelectric actuator configured to vibrate at a selected frequency, an ampoule configured to dispense a fluid through an aperture, and a vibrational transmission component defining a longitudinal axis and having an elongate section and a mounting section. The elongate section may define a lumen as it transitions from the mounting section, and the at least one piezoelectric actuator may be attached to the mounting section and the ampoule is removably attachable to the elongate section such that the aperture is aligned with the longitudinal axis when assembled.

In one method of use for emitting a fluid, the method may generally comprise securing an ampoule to a vibrational transmission component defining a longitudinal axis and having an elongate section and a mounting section such that an aperture defined by the ampoule is aligned with the longitudinal axis, actuating at least one piezoelectric actuator secured to the mounting section such that vibrations are transmitted from the mounting section, through the elongate section, and to the ampoule, and emitting a fluid from the ampoule and through the aperture.

In another embodiment of the ampoule, the ampoule may generally comprise an ampoule body having a cylindrical portion and a tapered portion which narrows into an opening defining an aperture which is in fluid communication with a volume defined by the ampoule body, and an insert having an outer surface which follows an inner surface of the ampoule body in a corresponding manner such that an annular capillary passage which is in fluid communication with the aperture is formed between the outer surface and inner surface.

BRIEF DESCRIPTION OF THE DRAWINGS

Having thus summarized the general nature of the invention and some of its features and advantages, certain preferred embodiments and modifications thereof will become apparent to those skilled in the art from the detailed description herein having reference to the figures that follow, of which:

FIG. 1A illustrates a perspective exploded view of a piezoelectric clamping actuator and an ampoule.

FIG. 1B illustrates a perspective view of the piezoelectric clamping actuator and ampoule secured by the actuator.

FIG. 2 illustrates a section end view of a piezoelectric clamping actuator.

FIG. 3A illustrates a section end view of a piezoelectric actuator in a bending mode while expending the clamp jaws as a result of harmonic analysis.

FIG. 3B illustrates a section end view of the piezoelectric actuator in a bending mode while contracting the clamp jaws as a result of harmonic analysis.

FIG. 4A illustrates a prospective view of an ampoule formed via a blow-fill-seal molding process.

FIG. 4B illustrates a front view of the ampoule formed by the blow-fill-seal molding process.

FIGS. 4C and 4D illustrate cross-sectional and side views, respectively, of the ampoule showing an insert that was included in the mold.

FIG. 4E illustrates a detail front view of another variation of an ampoule aperture formed in part from a separate tubular member.

FIG. 5A illustrates a perspective view of an ampoule secured within a piezoelectric clamping actuator which also includes a controller assembly having a drive circuit.

FIGS. 5B and 5C illustrate front and side views of the assembly having the ampoule and piezoelectric clamping actuator.

FIG. 5D illustrates a detail side view of the interface between the piezoelectric clamping actuator and the printed circuit board.

FIG. 5E illustrates a side view of the dispensing device aligned with an eye for treatment.

FIGS. 6A and 6B illustrate perspective views of an alternative embodiment of an actuator having a partially tubular component.

FIGS. 7A and 7B illustrate reversed detail perspective views of the elongate section and mounting section of the actuator.

FIGS. 8A and 8B illustrate side and perspective assembly views of the actuator.

FIGS. 9A and 9B illustrate alternate perspective views of an embodiment of a dispensing device utilizing the piezoelectric actuator assembly.

FIGS. 10A and 10B illustrate perspective and exploded assembly views of an alternative embodiment of a bimorph piezoelectric actuator and an ampoule holder component.

FIGS. 10C and 10D illustrate exploded assembly and perspective views of a piezoelectric actuator with a single piezo-ceramic plate.

FIGS. 11A and 11B illustrate perspective views of the piezoelectric actuator, ampoule, and cup and an alternative ampoule holder component.

FIGS. 12A and 12B illustrate exploded assembly and cross-sectional views of the ampoule.

FIGS. 13 and 14 illustrate exploded assembly and perspective views of a dispensing assembly and housing.

FIGS. 15 and 16 illustrate exploded assembly and perspective views of the housing, dispensing assembly, and ampoule.

FIG. 17 illustrates a side view of the dispensing device aligned with an eye for treatment.

FIG. 18 illustrates a perspective view of the dispensing device in use by a subject.

DETAILED DESCRIPTION OF THE INVENTION

The various embodiments of the invention described herein relates to a device for drug delivery to the ocular surface for treatment of ophthalmic diseases. In the systems and methods described herein droplets are dispensed in high frequency but in a single drop format or in a continuous stream depending on the electric signal input as described earlier. When droplets are produced they generally have ultra-small volumes ranging from about a few hundred pico-liters to about one nano-liters. Generally, droplets of such volume or a continuous (or discontinuous) collimated single stream do not cause blinking reflex.

The dispensing devices and clamping actuators described herein may be utilized with any of the embodiments described in further detail in the following references and in any combination: U.S. patent application Ser. No. 14/992,975 filed Jan. 11, 2016 (U.S. Pat. Pub. 2016/0199225); U.S. patent application Ser. No. 15/094,849 filed Apr. 8, 2016 (U.S. Pat. Pub. 2016/0296367), each of which is incorporated herein by reference in its entirety and for any purpose herein. Additionally and/or alternatively, although the devices and methods are described for ejecting droplets or a stream of fluid into or upon the surface of an eye for ophthalmic treatment, the devices and methods may be utilized for any number of non-ophthalmic applications as well, e.g., otologic (e.g. ear drum); endoscopic (e.g., gastrointestinal tract); gynecologic (e.g. cervical, uterine, reproductive care (fallopian tube)); laparoscopic (e.g., body cavity, abdominal); laryngoscopic (e.g., throat, vocal cords); bronchoscopic (e.g., bronchi or other lung tissue); urologic (e.g., bladder, prostate); oral (e.g., tonsils, dental, pharynx); neurosurgical (e.g., through skull drilled holes); dermatologic (e.g. local topical chemotherapy or chemical cautery).

For a device that is placed in a body cavity (such as an endoscopic, laparoscopic, or laryngoscopic device), the assembly may reside along a rigid or flexible/articulating shaft, with the piezoelectric actuator and the ampoule positioned distally so that it enters the body cavity, and power source positioned proximally and remain outside the body cavity, while the electrical current courses through the rigid or flexible shaft or flexible arm of the instrument to activate the piezoelectric actuator. In one embodiment, the ampoule resides next to the distal aspect of the light source and camera lens (e.g., adjacent to where the light arises out of the shaft and the camera lens is located). Alternatively, the assembly has no light source or camera and these elements are provided on a separate instrument. In another embodiment, the ampoule and piezoelectric actuator may remain on the proximal size of the shaft, such that the fluid being dispenses from the aperture courses through the length of the shaft and exits the distal end or tip of the shaft. The length of the rigid or flexible/articulating arm would differ in length and caliber/diameter depending on the application (e.g., relatively longer for laparoscopic, endoscopic, and gastroenterologic applications; relatively shorter for otologic applications; and intermediate for others).

The dispensing devices may advantageously utilize a disposable, removable, or separable drug or fluid package while desirably retaining the piezoelectric actuator or transducer for subsequent further uses, thereby providing an economical and cost effective approach with reuse of the piezoelectric actuator or transducer for further operation. Hence, in any of the embodiments described, the assembly may utilize a reusable actuator and/or housing with an ampoule which is separate or separable and implemented as a disposable or reusable ampoule. Alternatively, in any of the embodiments, the actuator and/or housing may be integrated with the ampoule in which case the entire assembly may be fully disposable or reusable. Various components of the assembly may be optionally reusable or disposable and implementation of such components is not intended to be limiting.

FIG. 1A and FIG. 1B illustrate an exploded perspective view and an assembly perspective view of one variation of the dispensing device assembly (1000). Device assembly (1000) may generally comprise a piezoelectric actuator assembly (1010) and a separable disposable fluid-filled ampoule (1020). The ampoule (1020) may comprise a thin-walled thermoplastic package which includes a second portion (1022) generally comprising a bulb or reservoir section and a first portion (1021) generally comprising a neck or an elongated section extending from the second portion (1022). The first portion (1021) may have a cylindrical shape with a circular or oval cross-sectional shape. Other cross-sectional shapes are also possible, e.g., triangular, square, pentagon, hexagon, octagonal, etc. One or more apertures (1023) are positioned on the wall of the first portion (1021).

The piezoelectric actuator assembly (1010) may generally comprise a piezoelectric clamping actuator (1014) which is configured to clamp or engage at least partially around the circumference of the first portion (1021) and adjacent to the one or more apertures (1023). Hence, the clamping actuator may have at least two opposed jaw members (1016A) and (1016B) which are designed to support and engage the first portion (1021) in a receiving channel (1011) defined between the jaw members (1016A), (1016B) via a secure engagement such as an interference fit, as shown in FIG. 1B. Once the first portion (1021) of the ampoule is engaged between the jaw members (1016A), (1016B) of the actuator assembly (1010), the assembly (1010) may also apply cycles of oscillations in the clamping direction against the wall of the ampoule as illustrated by the arrows (1014A) and (1014B). Oscillation of the ampoule first portion (1021) may cyclically deform the cross-section of the first portion (1021) so that the portion oscillates between, e.g., a circular shape and an elliptical shape to produce cycles of acoustic pressure in the fluid retained within the first portion (1021).

As shown, primary oscillations may be imparted by the jaw members (1016A), (1016B) to the first portion (1021) along a first direction (1030) such that a secondary oscillation is induced in the first portion (1021) along a second direction (1032) which is perpendicular to the first direction (1030). The primary and secondary oscillations may thus force the ejection of fluid (1024) retained within the first portion (1021) from the one or more apertures (1023) such that the emitted fluid (1024) may be ejected in a stream of individual droplets or as a continuous stream of fluid depending, e.g., upon the frequency of the oscillations. The emitted fluid (1024) may be ejected from the one or more apertures (1023) in a direction that is normal to a longitudinal axis of the assembly (1000) such that an initial angle of the fluid (1024) relative to the first portion (1021) is perpendicular relative to one another. Alternatively, the fluid (1024) may be emitted at some predetermined angle relative to the first portion (1021). In yet another alternative, multiple fluid streams may be emitted from different apertures simultaneously or sequentially which may each be at uniform angles or at angles different from one another, e.g., for emitting fluid streams at different regions of the eye when the assembly (1000) is maintained in a stationary position relative to the subject's eye.

Generally, the oscillation amplitude of the jaw members (1016A), (1016B) may be less than, e.g., 2 microns. As the fluid is emitted from the first portion (1021), the fluid retained within the second portion (1022) may provide for a continuous flow of the fluid into the first portion (1021) during use, where the fluid may then be emitted from the first portion (1021) in a continuous or discontinuous fluid stream. The first portion (1021) of the ampoule (1020) may be inserted into the piezoelectric receiving channel (1011) by a relatively light force, typically less than 10 Newton in some variations and less than 5 Newton in other variations.

Figure 2:
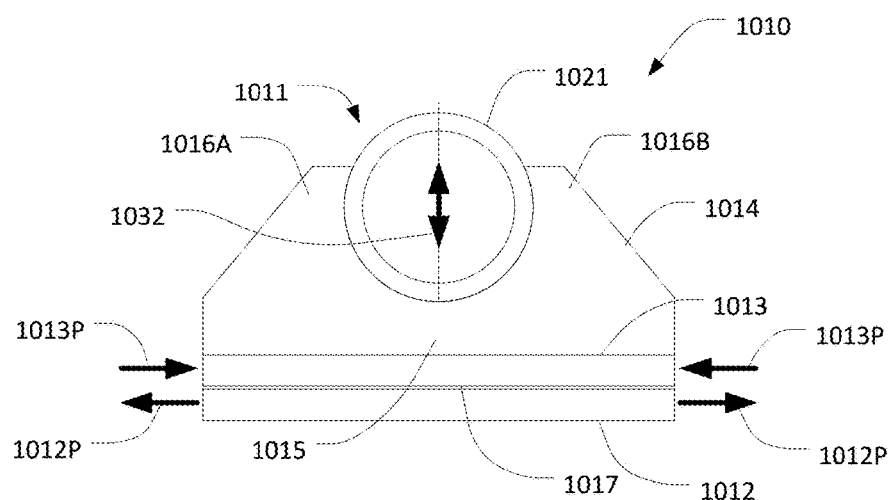

Referring now to FIG. 2, a cross-sectional end view of the piezoelectric actuator assembly (1010) and the first portion (1021) retained between the jaw members (1016A), (1016B) within the receiving channel (1011) is illustrated. The actuator assembly (1010) may have a base plate (1015) from which the jaw members (16A), (16B) extend into apposition relative to one another. In this variation, a first piezoceramic plate (1012) may be bonded to a second piezoceramic plate (1013) which may in turn be bonded to the base plate (1015). A passive layer (1017) may be optionally positioned between the two piezoceramic plates (1012) and (1013). Moreover, these two plates (1012), (1013) may be bonded to one another in a face-to-face manner such that each plate is oriented in an opposite polling direction. The size and configuration of the plates (1012), (1013) may be matched to one another as well as to the size and configuration of the base plate (1015) as well. Such a piezo laminate is also known as Bimorph Bender in that each piezoceramic plate (1012), (1013) expands and contracts in a direction opposite relative to each other. The variation shown illustrates how the first plate (1012) may be configured to expand planarly, as indicated by arrows (1012P), simultaneously when the second plate (1013) is configured to contract planarly, as indicated by arrows (1013P) so that the piezoceramic laminate oscillates resulting in a bending mode. The base plate (1015) may be attached to the piezoceramic laminate by a structural adhesive such as high strength epoxy or the like. In this way the bending of the piezo laminate causes the clamp member (1014) to bend which in turn causing the clamping jaws (1016A), (1016B) to cyclically apply a clamping force onto the first portion (1021) of the ampoule so that the fluid retained within is subsequently ejected from the aperture by the resulting secondary oscillations (1032).

Figures 3A, 3B:
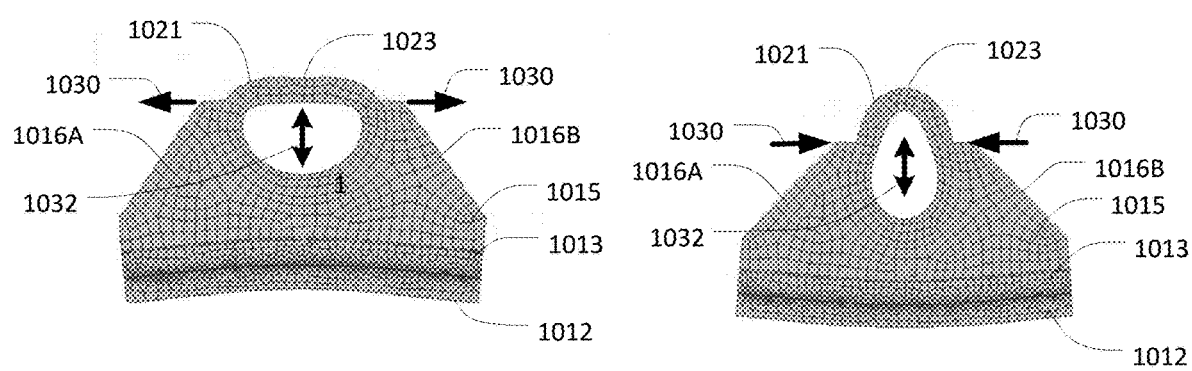

FIGS. 3A and 3B show the results of a harmonic analysis generated by finite element analysis to illustrate the frequency response of the clamping jaws (1016A), (1016B) and the first portion (1021) of the ampoule. The figures show that at an oscillation frequency of at least 22,000 Hz, the clamping jaws (1016A), (1016B) are actuated by the piezoceramic plates (1012), (1013) to oscillate in the direction shown (1030) to alternately squeeze down upon the first portion (1021) of the ampoule to force the circular cross-section into an oval or elliptical shape. Generally, in actuating the piezoelectric assembly, the operating frequency of the clamping jaws may be near or at its resonance frequency. For the purposes of illustration, the deflection of the ampoule has been scaled up by a factor of 4000. Analytical and actual measurement has shown that the amplitude of the first portion (1021) of the ampoule in the vicinity of the one or more apertures (1023) is only, e.g., about 1 micron. Actual measurement performed by laser vibrometer (Model Polytec Gmbh, Polytec Platz D-76337 Waldbronn).

In fabricating the ampoule (1020), the first portion (1021) and second portion (1022) may be constructed as separate components which are attached to one another or they may be constructed as a single, integrated structure. They may be made from one and the same material, or two different materials with differing material properties. For instance, the first portion (1021) may be made from a relatively more rigid material while the second portion made from a relatively more flexible material. The first (1021) and second (1022) portions may engage with each other in a variety of ways. For instance, a luer-lock mechanism maybe used to connect the first (1021) and second (1022) portions. In another example, a piercing mechanism or a screw-in mechanism may be used. In some mechanisms, fluid from the second portion (1022) may be released into the first portion (1021). One example for fabricating the ampoule (1020) is shown in the perspective view of FIG. 4A, which shows an ampoule (1020) which may be manufactured via a Blow-Fill-Seal molding process which includes a nozzle member that is inserted to the mold. Since the blow molding process has limited accuracy, small features such as the dispensing aperture may be difficult to produce by blow molding. Thus an insert member (1041) which includes the aperture may be separately manufactured using injection molding or laser drill techniques. The insert (1041) may be then placed inside the blow mold cavity and may be captured by the blow molded part during the blow mold process.

FIGS. 4A and 4B illustrate perspective and front views of the ampoule (1040) in its final shape following the blow molding process. FIG. 4D illustrates a side view of the final shape of the blow molded ampoule (1040). FIG. 4C illustrates a cross sectional side view of the ampoule showing the blow molded of the resulting ampoule and the insert member (1041) which was placed within the mold and captured by the blow molded ampoule. The insert (1041) may also include other features such as a valve or a vent. The blow molded ampoule may be generally made of, e.g., low density polyethylene (LDPE), high density polyethylene (HDPE), etc. while the insert member (1041) may be made of, e.g., Delrin® (E. I. du Pont de Nemours and Company) acetal homopolymer resin, polypropylene, etc.

With respect to the fabrication of the one or more apertures (1023), the formation of such small diameter apertures (e.g., on the order of 100 microns) may be relatively difficult because of behavior of thermoplastics when processed such as when laser machined. One variation may include the formation of a structure having the apertures separated from the ampoule fabrication so that the apertures may be formed with higher accuracy and precision. Such a structure may include the use of polyimide films which are stable over a wide range of temperatures such as Kapton® (E. I. du Pont de Nemours and Company). Other suitable polyimide materials may include, e.g., compositions of Kapton® and PTFE, synthetic polymers such as Nylon (E. I. du Pont de Nemours and Company), etc.

Figure 4E:
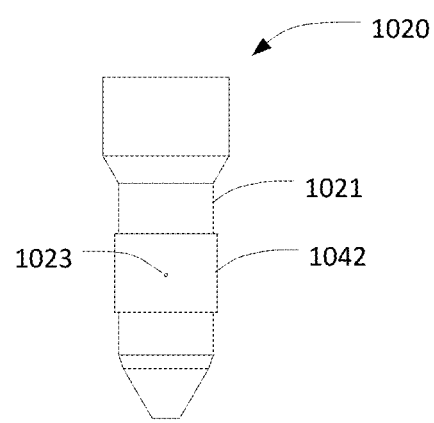

Referring to FIG. 4E, in some variations the first portion (1021) may include a thin-wall tubular member (1042) made from the polyimide such as Kapton® provided with one or more apertures (1023) where the tubular member (1042) may be fabricated separate from the ampoule and then secured, e.g., press-fit, over an external diameter of the first portion (1021) which defines a relatively larger opening. This opening may be covered by the tubular member (1042) to allow for fluid contact with the internal surface of the tubular member (1042) for fluid ejection through the aperture (1023). Because of the thermal stable properties of the tubular member (1042), the one or more apertures may be laser micro-machined and/or drilled. The tubular member (1042) may have an inside diameter of, e.g., 6 mm, and a wall thickness of, e.g., 0.1 mm, and one or more apertures (1023) with an exit opening of, e.g., 0.070-0.130 mm. The one or more apertures (1023) may be optionally tapered to provide for an efficient fluid ejection.

In other variations where multiple apertures are utilized for dispensing, each of the apertures may be configured to preserve the uniqueness of an individual stream rather than forming a mist. Factors such as aperture size and spacing between the apertures may be adjusted accordingly to maintain the formation of the individual streams of fluid and to minimize or inhibit the merging or conflation of the individual fluid streams. For instance, apertures each having a relatively larger size, e.g., 80-100 microns, may allow for both relatively shorter pulse durations to deliver an equivalent volume of fluid. Furthermore, apertures having such a size may also allow for the use of fluids having a relatively higher viscosity such as artificial tears which are generally comprised of methylcellulose or carboxy-methylcellulose, hyaluronic acid derivatives or other hydrogels which would otherwise block or clog smaller sized apertures in the range of, e.g., 10-12 microns.

The fluid or fluids which may be used with the dispensing device may vary to include any number of agents depending upon, e.g., the treatment, the region of the body where the fluid is applied, etc. Examples of various fluids or agents which can be used may include (but are not limited to), e.g., anti-infectives (including but not limited to antibiotics, antivirals, etc.); anti-inflammatories (including but not limited to steroids and non-steroidal anti-inflammatory drugs (NSAIDS), etc.); anti-allergy (including but not limited to anti-histamines and mast cell stabilizers, etc.); anti-fungals; vasoconstrictors; mydriatic (pupil dilating) agents; miotic agents (pupil constricting agents); biologics (e.g. proteins, engineered proteins, etc.); small molecules; anesthetics; analgesics; intraocular pressure lowering agents (including but not limited to prostaglandin analogs, ROK inhibitors, beta blockers, carbonic anhydrase inhibitors, and alpha agonists, etc.); lubricants (including but not limited to saline, polymer solutions, proteoglycans, glycosaminoglycans, carbohydrates, etc.); iodine derivatives; etc. and/or various combinations thereof. Additional drugs and agents which may be utilized with the devices described may include any number of the agents disclosed in further detail in U.S. Pub.

2017/0344714 and U.S. Pat. No. 9,087,145 which are each incorporated herein by reference and for any purpose.

The dispensing device assembly (1000) including the ampoule (1020) and actuator assembly (1010) may be controlled via a controller which may include a platform or substrate upon which the actuator assembly (1010) may be positioned. FIG. 5A illustrates a perspective assembly view of an alternative clamping transducer assembly (1200) in which the actuator assembly (1010) may be mounted directly on a printed circuit board (PCB) (1005) which includes a circuit section (1005C) at a first end and a piezo mounting section (1005P) at a second end where the actuator assembly (1010) may be mounted. Hence, when the first portion (1021) of the ampoule (1020) is secured within the clamping assembly (1014), the components may form an assembly supported upon the PCB (1005). A piezoelectric driver circuitry (1051) mounted on the PCB (1005) in the circuit section (1005C) may comprise, e.g., a programmable processor, which is in electrical communication with the actuator assembly (1010) to control the actuation and ejection of the fluid contained within the ampoule (1020).

As previously described, the piezoelectric clamp (1014) may include the first piezoceramic plate (1012) bonded to the second piezoceramic plate (1013) where the first piezoceramic plate (1012) may be mounted on to the PCB (1005) along the piezo mounting section (1005P) and the clamp (1014) may be structurally bonded to the face of the second piezoelectric plate (1013). Both piezoceramic plates (1012) and (1013) may be aligned relative to each other and the combination of the piezoceramic plates (1012) and (1013) and the PCB (1005) may form a laminate which known as bimorph bender and which oscillates in a bending mode thereby causing oscillator clamping action on clamp (1014) electrically configure to oscillate in a bending mode, as described herein, so that the droplets or stream of fluid (1024) are ejected from the one or more apertures (1023).

In another variation, the first piezoceramic plate (1012) may be mounted on a first or back side of the PCB (1005) and the second piezoceramic plate (1013) may be mounted on a second or front side of the PCB (1005) so that the PCB (1005) is sandwiched between the respective plates (1012), (1013). The clamp (1014) may be mounted upon the second piezoceramic plate (1013), as previously described, and the plates (1012), (1013) may remain aligned relative to one another. In one variation, the piezoceramic plates (1012), (1013) may be soldered to the PCB (1005) during the solder reflow process in which all the electronic components (1051) are assembled. In this variation, the PCB (1005) functions as a passive layer and collectively forms the bimorph bender, as shown in the side and detailed side views of FIGS. 5C and 5D. Either mounting configuration, where the plates (1012), (1013) are mounted to one another directly and then to the PCB (1005) or where the PCB (1005) is sandwiched between the plates (1012), (1013), may be utilized with any of the ampoule (1020), PCB (1005), controller, and/or housing variations described herein.

The piezo mounting section (1005P) of the PCB (1005) may be at least partially isolated from the circuit section (1005C) by one or more cutouts. Referring now to the front view of FIG. 5B, cutouts (1052), (1054), (1053), (1055) may extend transversely inward from the outer edge of the PCB (1005) and define channels or notches positioned, e.g., proximally and distally, of the piezo mounting section (1005P). The cutouts (1052), (1054), (1053), (1055) may at least partially isolate, prevent, or limit the transmission of vibrations from the piezo mounting section (1005P) to the rest of the PCB (1005) and the circuit section (1005C). In other variations, instead of cutouts, other vibration dampening mechanisms may be used to vibrationally isolate the piezo mounting section (1005P). The electronics may be hermetically sealed and/or isolated from the mechanical portions of the devices not only to isolate vibrations from the electronics but also to protect the electronics from fluids, debris, etc.

Figure 5E:
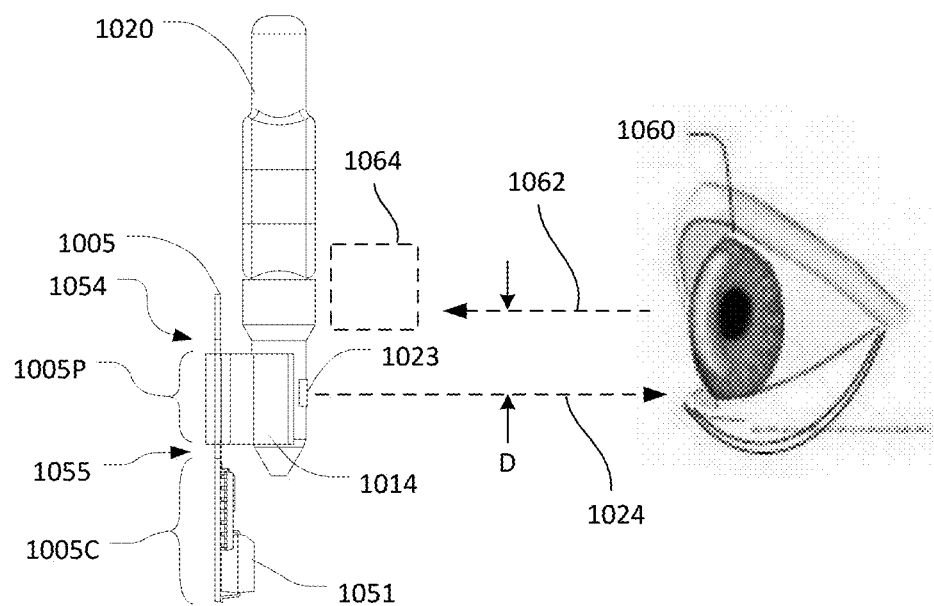

As described herein, the fluid ejection device may include an optical alignment mechanism which helps to align or target the one or more apertures to the ocular surface or to the area of the lower conjunctiva prior to actuation to ensure that the entire dose reaches the surface of the eye. For instance, FIG. 5E illustrates a side view of the actuator assembly with an exemplary alignment mechanism (1064) positioned relative to the eye (1060) of a patient. The alignment mechanism (1064) may include any of the variations described herein or any number of other optical alignment devices which may be used with the actuator assembly. The housing is not illustrated for clarity purposes only.

Prior to ejecting the fluid, the user may align the eye (1060) to be treated with the alignment mechanism (1064) so that the device is brought to an alignment with the optical axis (1062) of the eye (1060) to be treated or the center of the pupil. Proper alignment with the optical axis (1062) may accordingly position the one or more apertures (1023) at a predetermined small offset (D) relative to the optical axis (1062) as shown, e.g., 4 to 12 mm, depending on the preset offset (D). When the device is actuated, a stream of fluid (e.g., a continuous stream or discontinuous stream of droplets) will reach the targeted surface of the eye (1060) or the conjunctival tissue and deposit fluid at the above mentioned offset (D) from the pupil.

Figure 6A:
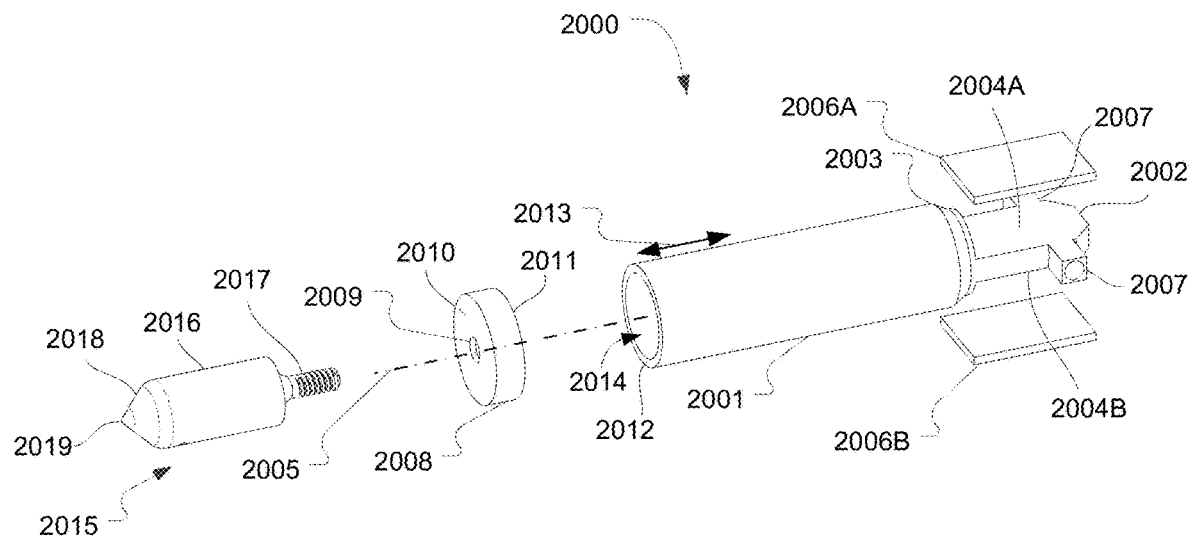

In yet another alternative embodiment of an actuator (2000), a transducer assembly configured to oscillate a disposable drug ampoule (2015) to dispense a fluid from the ampoule is illustrated in the exploded perspective view of FIG. 6A. The assembly may be used to dispense a fluid to, e.g., the corneal surface of the eye or other region of the patient body. This embodiment may comprise a vibrational transmission component having an elongate section (2001) formed as, e.g., a partially tubular component, extending distally from a transducer mounting section (2002) generally configured into, e.g., a rectangular section. The two sections (2001) and (2002) may blend into each other via a junction (2003) which may form a tapered or stepped transition between the two.

The junction (2003) may project radially from the mounting section (2002) to transition and form the elongate section (2001), as mentioned above, which further extends longitudinally and symmetrically about the longitudinal axis (2005) to terminate at a flattened interface surface (2012) which is formed perpendicularly relative to the axis (2005). The entire assembly (2001), (2002), (2003) may be formed of a thermoplastic material preferably with modulus of elasticity that is greater than, e.g., 3 GPa, such as acrylic, Acrylonitrile butadiene styrene (ABS), polyaryletherketone (Peek), etc. The assembly may be optionally formed (e.g., machined, cast, etc.) of a metal as well.

The transducer mounting section (2002) may be formed with flattened mounting surfaces (2004A) and (2004B) which are aligned symmetrically and in parallel relative to one another and relative to a longitudinal axis (2005) of the transducer assembly (2000). The piezoelectric plates (2006A) and (2006B) may be similarly or identically sized with one another and are mounted on opposite sides from one another. The mounting section (2002) may further include one or more mounting projections (2007) which extend from one or both sides of the section (2002) to facilitate securement of the assembly (2000) when in use.

The mounting arrangement of the piezoelectric plates (2006A) and (2006B) is advantageous since the transducer assembly (2000) can be made of a thermoplastic material which can optionally provide for a relatively low-cost disposable product. Conventional longitudinal transducers, such as those described in U.S. Pat. Nos. 4,655,393; 4,352, 459; and U.S. Pat. Pub. 2010/44460 are typically made of a metal such as aluminum or stainless steel. Each of these references is incorporated herein by reference in its entirety and for any purpose herein. These transducers often have a clamping feature which clamps the piezoelectric plates to the end face of the transducer shaft. i.e., the planer surface of the piezoelectric plate is perpendicular to the axis of the transducer, and such arrangements have the transducers incorporate a clamping screw to secure the piezoelectric plates. However, it has been found that a thermoplastic material under a clamping stress tends to creep over time and consequently the preload force is relaxed and the function of the transducer deteriorates over time. Hence, the piezoelectric plates (2006A) and (2006B) may be simply adhered to their respective mounting surfaces (2004A) and (2004B) via an adhesive rather than using a clamping force provided that any discontinuities in the interface between the plates (2006A) and (2006B) and the surfaces (2004A) and (2004B) are minimized. The advantage of using a plastic transducer assembly may be a significant reduction in manufacturing costs since the plastic can be molded to any desirable shape very inexpensively and entirely removes the need for clamping of the plates (2006A), (2006B).

The elongate section (2001) may extend and form a tubular member which defines a uniform wall thickness, as shown. The section (2001) may be partially hollow and define a lumen (2014) as it transitions from the mounting section (2002) and junction (2003). While the elongate section (2001) shown may be formed as a tubular section, other cross-sectional shapes may be used as well, e.g., elliptical, octagonal, hexagonal, pentagonal, rectangular, etc. and the length of the section (2001) may range anywhere from, e.g., 1 to 10 cm. However, when the section (2001) is formed as a tubular member, this cross-sectional shape may be optimal for transferring vibrations from the piezoelectric plates (2006A) and (2006B) and through the length of the section (2001).

An ampoule mounting element (2008) may be configured to be mounted upon a distal end of the elongate section (2001) such that a first proximal side (2011) of the element (2008) contacts against and/or over the interface surface (2012) and a second distal side (2010) of the element (2008) is presented for interfacing against the ampoule (2015). The element (2008) may further define an ampoule engagement feature (2009) for coupling with the ampoule (2015). In one particular embodiment, the element (2008) may be formed into a cup-shaped member that is connected via the proximal side (2011) to the end of the elongate member (2001). An inner diameter of the cup-shaped configuration may engage securely over the distal end of the elongate section (2001), e.g., via an interference fit or any other securement mechanism. The ampoule engagement feature (2009), in this embodiment, may be formed as a threaded opening which is aligned with the longitudinal axis (2005).

Turning now to the ampoule (2015), a proximal end of the ampoule (2015) may be formed as an engagement rod (2017) which extends proximally from the body (2016) of the ampoule (2015). The rod (2017) may be threaded allowing for an optionally threaded engagement with the ampoule engagement feature (2009) of the ampoule mounting element (2008). This may allow for the secure threaded engagement of the ampoule (2015) to the mounting element (2008) and the ready removal and replacement of the ampule (2015) from the assembly (2000), e.g., for replacement when the ampoule (2015) is emptied after use. Other embodiments of the ampoule may utilize other attachment features rather than a rod (2017), e.g., frictional fitting, magnetic coupling, etc.

The ampoule (2015) may further include a distal tapered section (2018) which narrows from the body (2016) to a distal end defining an opening (2019) through which fluid or agent contained within the ampoule (2015) may be dispensed during use of the assembly (2000). The reservoir volume of the ampoule (2015) may also vary anywhere from, e.g., 0.2 ml to 5 ml or more preferably 0.5 ml to 1.5 ml, although other volumes may be sized accordingly.

Figure 6B:
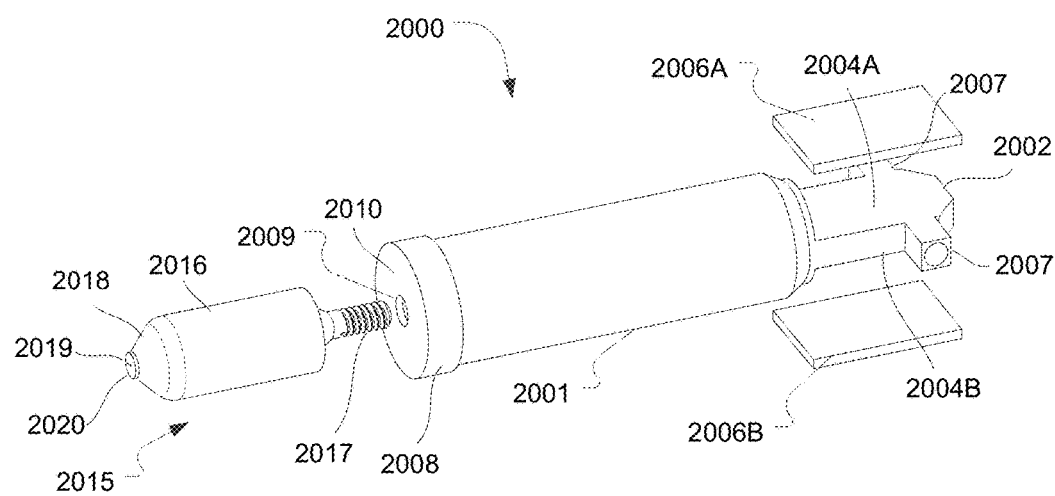

FIG. 6B shows a perspective view of the assembly (2000) which is partially assembled. The mounting element (2008) is shown attached to the distal end of the elongate section (2001) and ready to receive the engagement rod (2017). In this embodiment, the ampoule (2015) is illustrated with a flattened distal portion (2020) through which the dispensing aperture (2019) is defined.

Figure 7A:
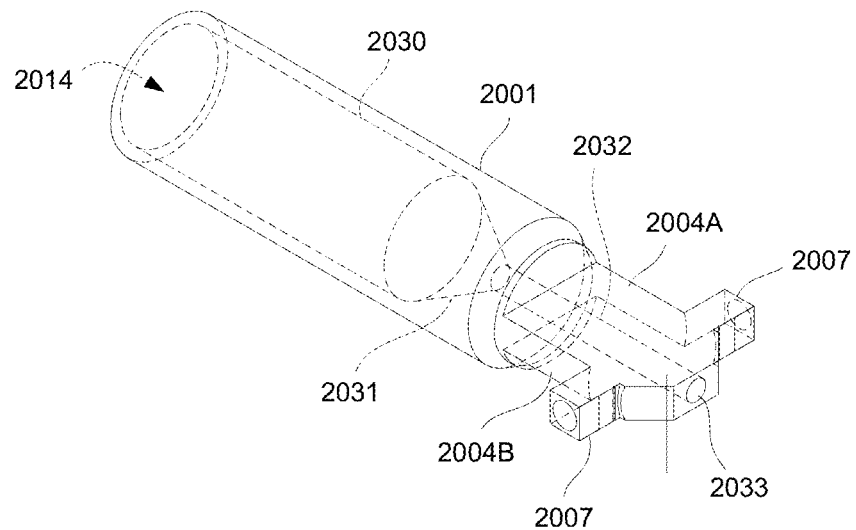
Figure 7B:
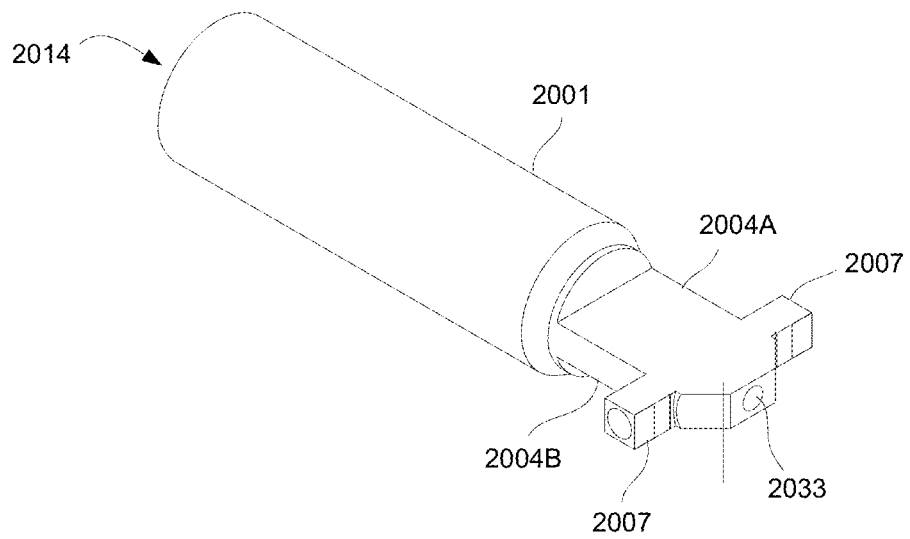

FIGS. 7A and 7B show reversed detail perspective views of the elongate section (2001) and mounting section (2002). The FIG. 7A shows a transparent view of the assembly for clarity purposes. As illustrated, the elongate section (2001) may have the lumen (2014) defined at least partially through the interior of the section (2001) such that an inner wall (2030) is defined within and narrows or tapers along a conical region (2031) through a proximal portion of the elongate section (2001) to a second lumen (2032) which is smaller in diameter than the lumen (2014). This second lumen (2032) may extend through the mounting section (2002) and terminate at an opening (2033) defined at a proximal end of the section (2002). This lumen may provide a channel into the lumen (2014) to provide for the drainage of any fluids which may have leaked and also prevents a pressure differential from building within the lumen (2014) when the assembly is vibrating.

Figure 8A:
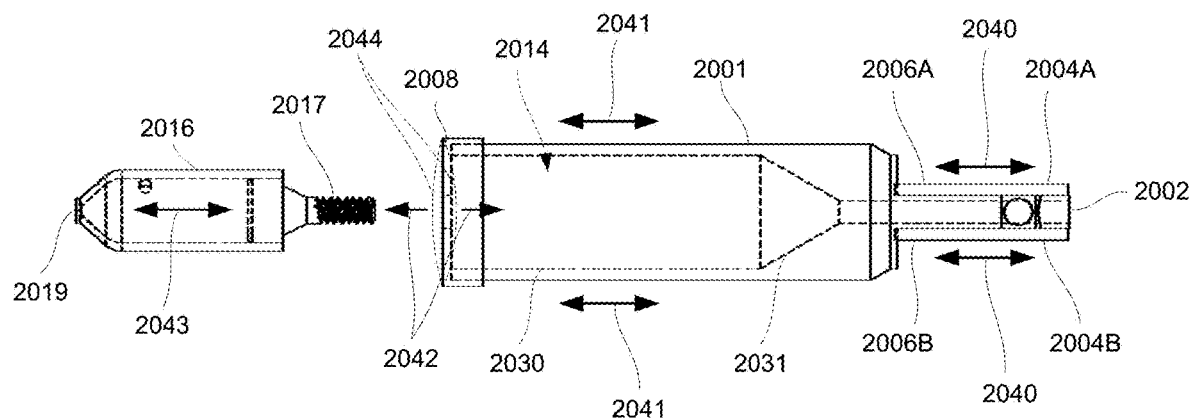

During use and with reference to FIG. 8A, which illustrates a side view of the assembly, the two piezoelectric plates (2006A), (2006B) may be seen symmetrically aligned and in parallel relative to one another. Because the plates (2006A), (2006B) are configured to have the same polarity orientation and electrical connection, the two plates (2006A), (2006B) will expand and contract simultaneously in the same direction and without a phase shift between the plates (2006A), (2006B), as indicated by the vibrational direction (2040). In this way, stress is developed in the mounting section (2002) under the plates (2006A), (2006B) when the plates (2006A), (2006B) are actuated to vibrate via a pulse generator (as described herein) at a frequency that is equal to a natural longitudinal frequency of the elongate section (2001). This vibration is transmitted through the mounting section (2002), junction (2003), and to the elongate section (2001). As a result, the stress propagates back and forth through the cylindrical walls of the elongate section (2001) according to acoustic wave propagation principles and the elongate section (2001) vibrates at a relatively high amplitude extending and contracting along its longitudinal axis (2005) as indicated by the vibrational direction (2041). Because the elongate section (2001), mounting section (2002), and junction (2003) may be fabricated from a single material such that they form an integral piece, the oscillations may propagate through the device relatively unimpeded.

Because the ampoule mounting element (2008) is securely attached to the distal end of the elongate section (2001), the face of element (2008) may be forced to resonate substantially at the same resonant frequency of the elongate section (2001). At its natural frequency, the face of the element (2008) may vibrate in a bending mode such that the amplitude near the circumference of its annular opening (2009) is the highest over the element (2008) as indicated by the vibrational direction (2042) and phantom lines (2044) which indicate the displacement movement of the element (2008) relative to the elongate section (2001).

Figure 8B:
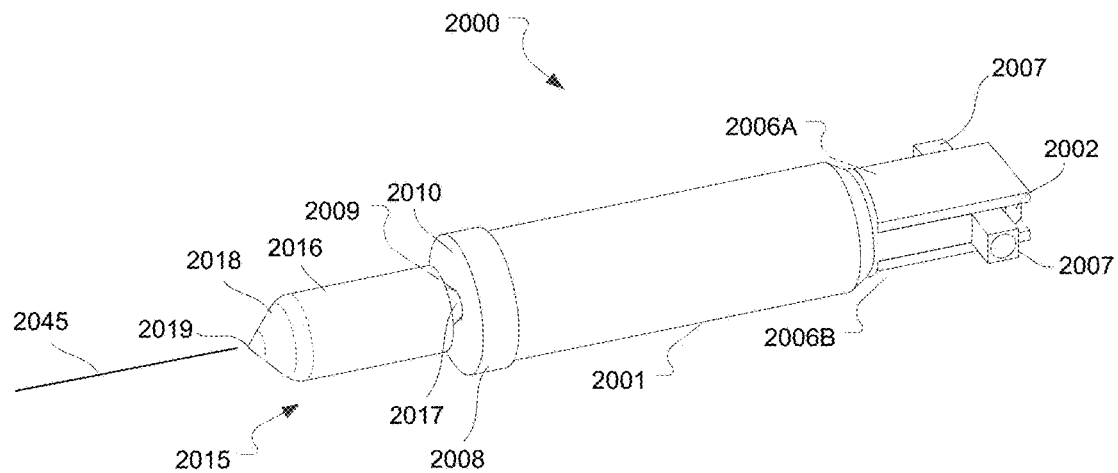

Advantageously, the ampoule may be attached at the opening (2009) via rod (2017) such that the oscillation (2042) at its highest amplitude is transmitted to the body (2016) of the ampoule resulting in the corresponding oscillation (2043) of the ampoule body (2016). Consequently, the fluid contained within the ampoule (2015) may be ejected out of the ampoule body (2016) and through the aperture (2019) into a stream (2045) of fluid, as shown in the perspective view of FIG. 8B, for treating the eye of the patient or other region of the patient's body. Depending upon the frequency generated by the pulse generator, the stream (2045) may be ejected as a stream of individual droplets which are collinearly aligned when dispensed. If the pulse generator generates a frequency above a threshold frequency, the stream (2045) may be configured such that the individual droplets are coalesced into a single continuous stream of fluid.

Figure 9A:
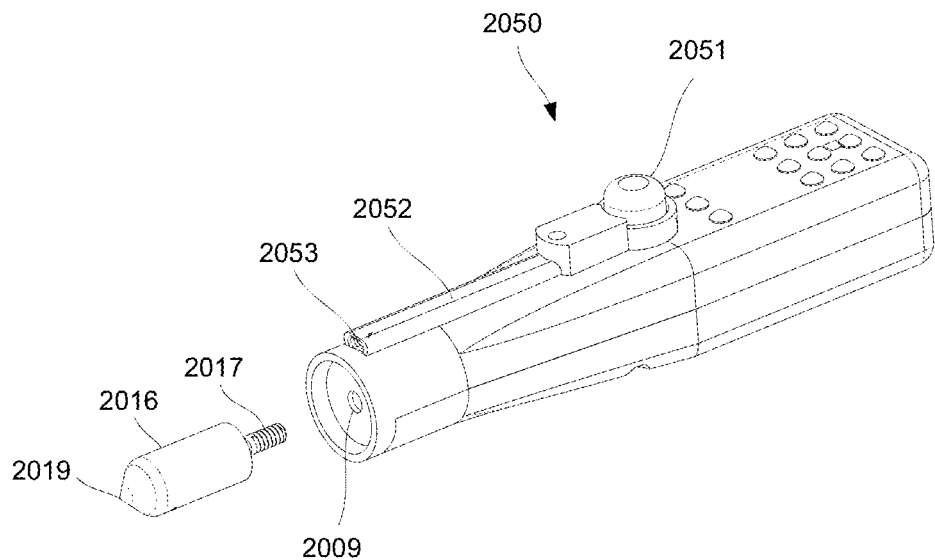
Figure 9B:
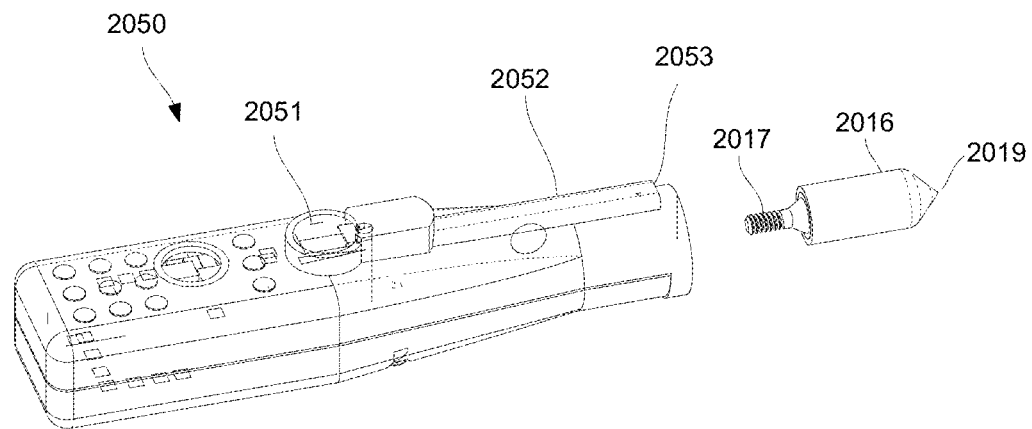

FIGS. 9A and 9B illustrate alternate perspective views of an embodiment of a dispensing device (2050) utilizing the piezoelectric actuator assembly (2000). The assembly may be encased within the device housing with the annular opening (2009) exposed at a distal end of the device (2050). The ampoule rod (2017) may be inserted or otherwise attached to the device (2050) via the annular opening (2009), as described above. Once the ampoule has been suitably attached and seated, the ampoule dispensing aperture (2019) is brought into alignment with the bore (2053) of light source (2052) by an offset distance. As described herein, while the bore (2053) of light source (2052) is aligned with the optical axis of the eye or the center of the pupil, the dispensing aperture (2019) is offset by the predetermined distance below the optical axis of the eye, e.g., 2-20 mm. Thus, when the device (2050) is actuated, e.g., by manipulating one or more controls (2051), the dispensed stream of fluid may be ejected to reach the area of the eye below the optical axis for treatment.

Figure 10A:
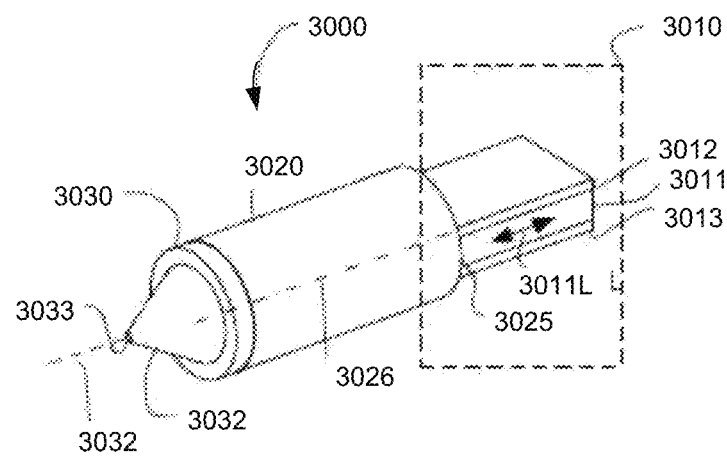
Figure 10B:
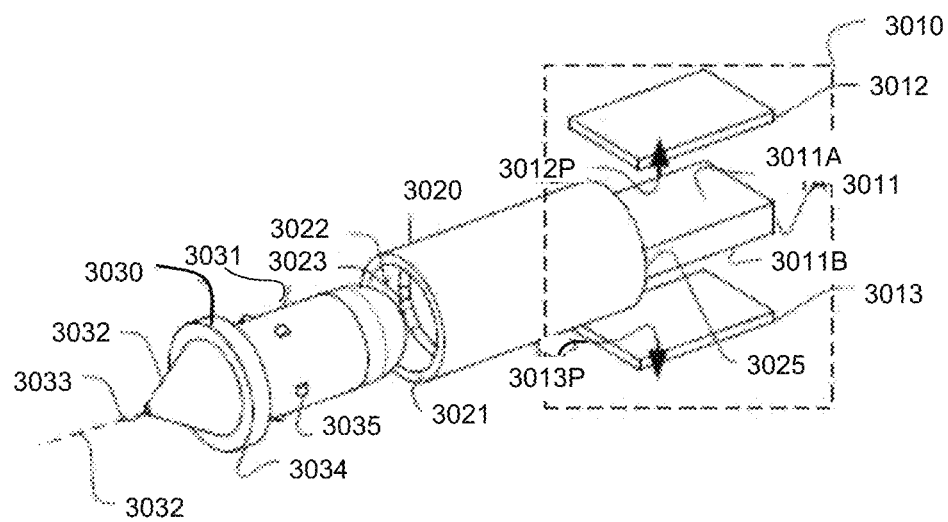

In yet another embodiment of the transducer assembly, FIGS. 10A and 10B illustrate perspective and exploded perspective views of a piezoelectric transducer (3000) which functions similarly to the embodiments described above. Transducer (3000) comprises a bimorph actuator (3010) which includes an ampoule holder (3020) which may retain and hold an ampoule (3030) containing a fluid to be dispensed. Ultrasonic oscillations which are generated by the bimorph actuator (3010), as described herein, may propagate to the ampoule holder (3020) and to the ampoule therein which in turn produce cycles of acoustic pressure in the fluid and ejection of droplets (3032) from an aperture (3033) at the tip of the ampoule.

The bimorph actuator (3010) may comprise a laminate of one passive plate (3011) and two active piezo-ceramic plates (3012), (3013) configured such that the passive plate (3011) is laid in between the two piezo-ceramic plates (3012), (3013), one piezo-ceramic plate on each opposite side of the passive plate. The faces of the passive plates (3011A) and (3011B) may be attached or bonded to a face of one piezo-ceramic plate (3012) and to a face of one piezo-ceramic plate (3013), respectively, while the passive plate itself is extended as a cantilever plate from the ampoule holder (3020) via a junction interface (3025). Oscillation of piezo-ceramic plates (3012), (3013) are transmitted to the passive plate (3011) and to the ampoule holder via a connection therebetween, as will be explained further below.

In one embodiment, both piezo-ceramic plates (3012), (3013) may have the same piezo poling orientation as indicated by the arrows (3012P), (3013P) relative to their attachment to the passive plate and the same electrical connection with respect to the piezo poling such that when the two piezo-ceramic plates receives alternating voltage signal, accordingly, bimorph actuator (3010) expands and contracts along its lateral dimension and producing oscillation amplitude in the lateral directions as indicated by arrows (3011L). Lateral oscillations are transmitted to the ampoule holder (3020) via the attachment between the structural plate and the ampoule holder (3020).

This embodiment, similar to the piezo-ceramic plate configuration described above, illustrates the use of two symmetrically attached plates; however, in other embodiments, fewer than two or greater than two plates may be utilized. Additionally, it is within the scope of this description that other variations of the plates may be used having different configurations, as desired.

The frequency of the alternating electrical signal is substantially equal to the resonance frequency of the dispensing device at its lateral or longitudinal mode. In one embodiment, the length of the bimorph actuator (3010) may be, e.g., 15 mm, and its width may be, e.g., 10 mm. The passive plate may be an integral part to the ampoule holder wherein the overall length of the piezoelectric actuator (3010) may be, e.g., 35 mm, and the diameter of the ampoule holder may be, e.g., 8-12 mm. The resonance frequency of the piezoelectric actuator may be, e.g., 22.5 kHz. The passive plate (3011) may extend for the ampoule holder perpendicularly as a cantilever plate or optionally the passive plate may extend at an angle relative to the longitudinal axis (3026) of the ampoule holder.

The ampoule (3030) that can be readily attached to or detached from ampoule holder (3020) as will explain further below. Referring to FIG. 10B it can be seen that ampoule (3030) may have a cylindrical shape (3031) which transitions to a conical shape (3032) so that it tapers from the body of the ampoule (3030) to a relatively smaller opening (3033) defining the exit opening of dispensing aperture. Ampoule (3030) may further include a flange (3034) at the end of the cylindrical body that is used to engage with the ampoule holder (3020) to receive ultrasonic oscillation from the ampoule holder (3020) when flange (3034) is held against the face (3021) of ampoule holder (3020). This flange (3034) may be integrated with the body of the ampoule (3030) to ensure that no interface between the two is formed although in other variations, the flange (3034) may be formed as a separate component and securely attached to the ampoule (3030) body.

The ampoule (3030) may further include a circular array of protrusions or bumps (3035) arranged around the circumference of the ampoule (3030) at a small distance from the face of flange (3034), typically from, e.g., 1 to 4 mm. The protrusions (3035) may be used as anchoring points to securely retain the ampoule (3030) inside the ampoule holder (3020). These protrusions or bumps may also be shaped in any number of different configurations as well as arranged in any number of patterns so long as the protrusions (3035) securely retain the ampoule (3030) within the ampoule holder (3020).

Ampoule holder (3020) includes an end-face (3021) and an internal bore (3022) having a diameter that is slightly larger than the diameter of the ampoule. The internal bore may have a hump or restricting feature (3023) around its internal diameter that may be shaped, e.g., like a rounded circumferential protuberance. When ampoule (3030) is inserted into the ampoule holder (3020), the flange (3034) may engage with the end-face (3021) as protrusions (3035) partially cross over hump (3023). In the way, the ampoule (3030) may be clamped securely to the end face of the ampoule holder and ultrasonic oscillation may be therefore transmitted effectively. FIG. 10A shows an illustration of the ampoule (3030) as it is retained within the ampoule holder (3020). Generally, the inserting force of the ampoule (3030) into the ampoule holder is below, e.g., 5 N.

Figure 10C:
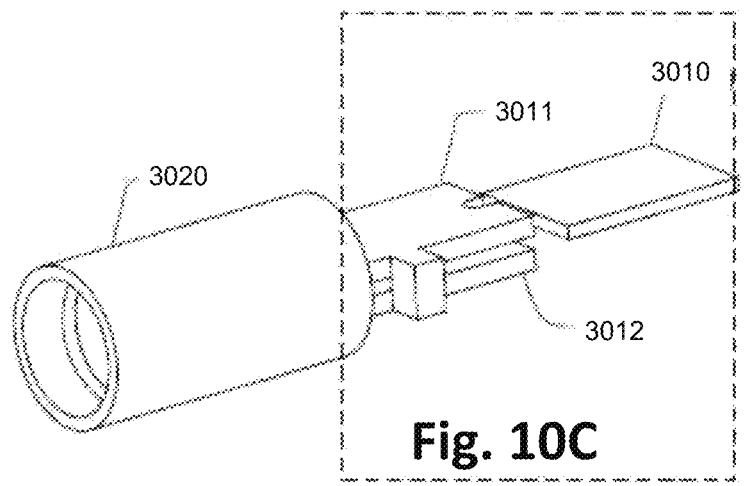
Figure 10D:
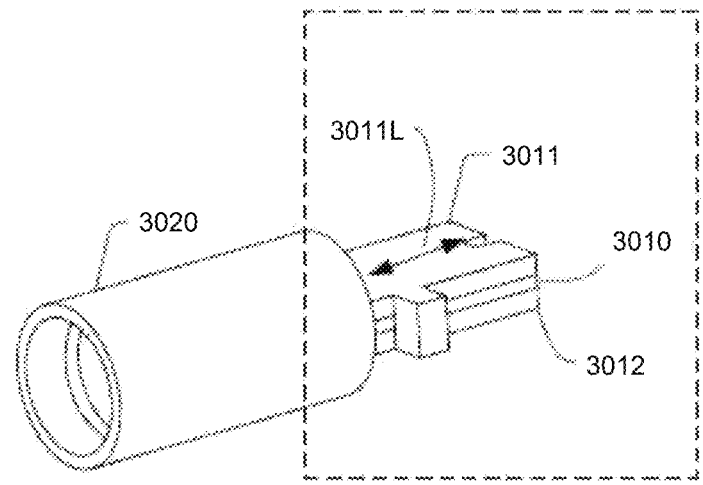

FIGS. 10C and 10D illustrate an alternative piezoelectric transducer that uses an actuator with a single piezo plate and two passive plates. As illustrated, actuator (3010) may comprise a laminate of a single piezo-ceramic plate (3010) and two passive plates (3011), (3012) configured such that the piezo-ceramic plate (3010) is laid in-between the two passive plates (3011), (3012), one passive plate on each side of the piezo-ceramic plate. The faces of the passive plates (3011), (3012) in contact with the opposite sides of the piezo-ceramic plate (3010) may be attached or bonded to faces of the piezo-ceramic plate (3010) while the two passive plates (3011), (3012) are structurally connected to the ampoule holder (3020). Oscillations of the piezo-ceramic plate (3010) are transmitted to the passive plates (3011), (3012) and to the ampoule holder (3020) via a connection therebetween. In one embodiment, the frequency of the alternating electrical signal is substantially equal to the resonance frequency of the dispensing device at its lateral or longitudinal mode. Additionally, in this variation, the piezo-ceramic plate (3010) may be mounted along the longitudinal axis of the ampoule holder (3020) so that the two passive plates (3011), (3012) are symmetrically aligned relative to the longitudinal axis.

As illustrated, actuator (3010) may include one or two piezo-ceramic plates and one or two passive plates. In the present embodiment, the passive plates may be made of thermoplastic elastomers, e.g., acrylic or PEEK. Elastomers have a relatively low modulus of elasticity, approximately 3 GPa, relative to the elasticity of the piezo-ceramic material having a modulus of elasticity of approximately 60 GPa. This subsequently enables the use of relatively thinner piezo-electric plates to generate cycles of structural deformation. Thinner piezo-ceramic plates require proportionally lower input voltages which substantially eliminates the need to include a voltage boosting circuitry such as DC-DC converter. Thus making lateral longitudinal transducers from thermoplastic as described reduces the cost of the electronic circuit and subsequently the product itself. The lateral or longitudinal transducer and ampoule holder may be made from a thermoplastic by, e.g., injection molding processes, with thermoplastics having a modulus of elasticity that is lower than, e.g., 4 GPa, and more preferably between, e.g., 3 GPa to 4 GPa, while the thickness of the piezo-ceramic plate may be less than, e.g., 1 mm, and preferably less than, e.g., 0.5 mm.

Figure 11A:
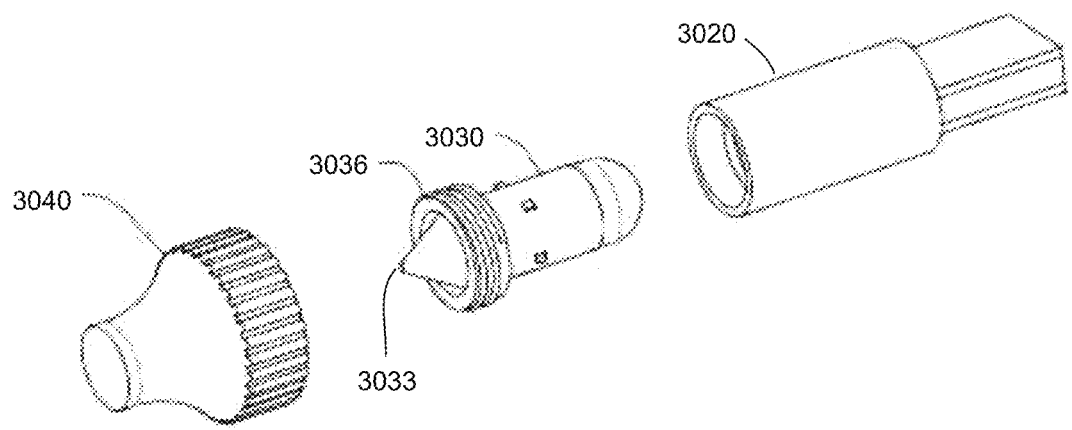
Figure 18:
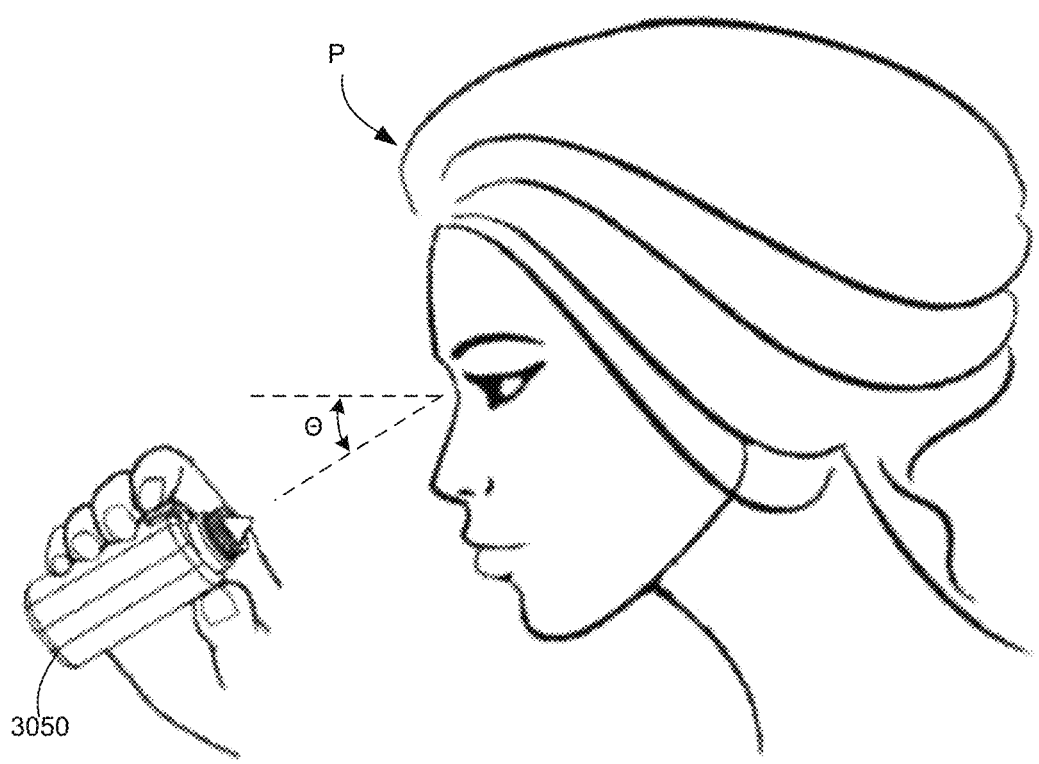

Referring now to FIG. 11A, it can be see that ampoule (3030) may include a cup or cap (3040) that seals off the opening of aperture (3033) during storage and periods on non-use. The cup or cap (3040) may be configured to be engaged with an external thread (3036) or other feature or it may be retained via the ampoule holder (3020). The ampoule (3030) may dispense fluid in any orientation thereby allowing the user (P) to conveniently position his/her head, e.g., inclined downwardly towards the ground, while the dispensing device (3050) is inclined at an angle such as being inclined upwardly at an angle (0), as illustrated in FIG. 18, relative to horizontal. In this position the liquid that is stored in the ampoule may move away from the aperture due to gravity; however, in the present embodiment, the ampoule (3020) may include a capillary feature that draws fluid directly to the aperture regardless of the ampoule (3020) orientation and fluid level within.

Figure 11B:
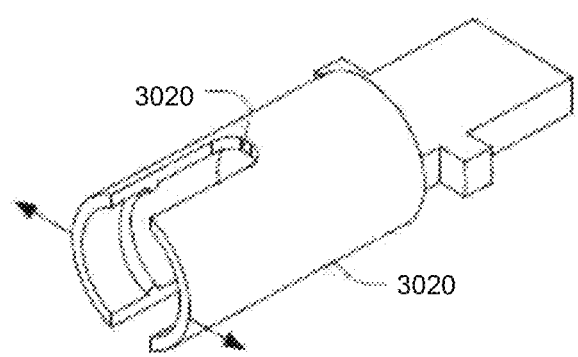

FIG. 11B shows a perspective view of another variation of the ampoule holder (3020) which may define grooves or channels along the sides of the holder (3020) to accommodate expansion of the holder (3020), as indicated by the arrows. When an ampoule (3030) is inserted or removed from the holder (3020), the opposing sides of the holder (3020) may extend radially due to the presence of the grooves or channels to accommodate the securement or release of the ampoule (3030).

Figure 12A:
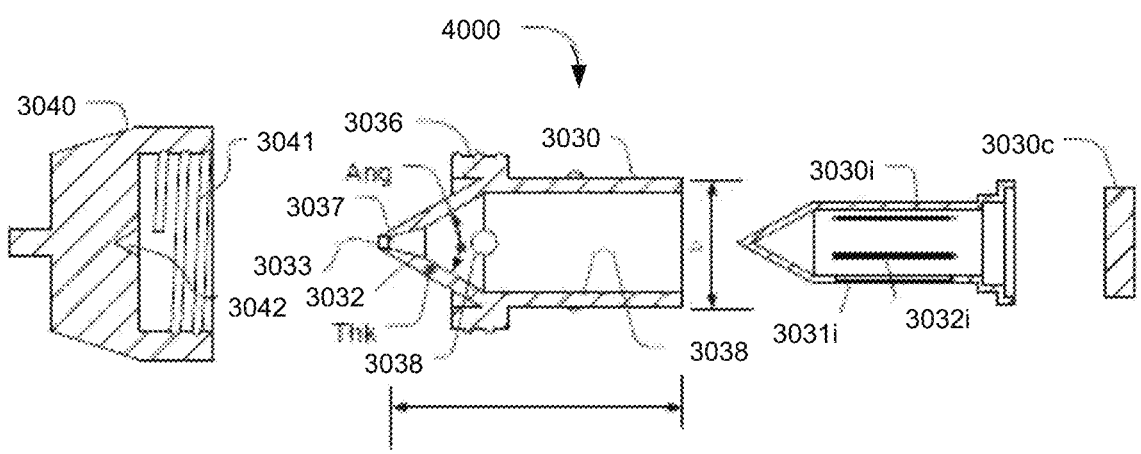
Figure 12B:
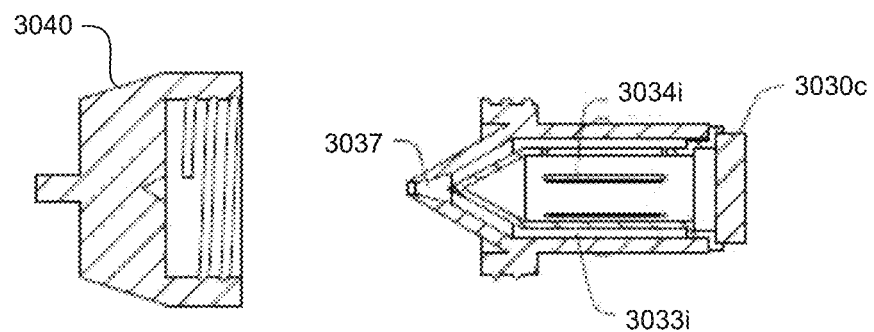

FIGS. 12A and 12B illustrate exploded assembly and cross-sectional side views of ampoule assembly (4000). It can be see that ampoule assembly (4000) comprises a hollow cylindrical body (3030) that transitions to a conical shape (3032) which tapers from the cylindrical body to a narrow opening (3033) which defines the exit of the dispensing aperture (3037). The ampoule further includes an insert (3030$i$) that may be placed inside the ampoule (3030) and forms a gap between its external surfaces (3031$i$) and the internal surfaces (3038) of ampoule (3030). The insert (3030$i$) may have a shape which corresponds with the internal shape or volume defined by the ampoule (3030) but which is slightly smaller so that a body of the insert (3030$i$) may be similarly cylindrical and which tapers into a conical configuration. FIG. 12B illustrates a cross-sectional view of the ampoule (3030) when insert (3030$i$) is placed inside the ampoule (3030). It can be seen that a gap (3033$i$), e.g., typically of 0.3 to 1 mm, is formed between the two surfaces such that the insert (3030$i$) outer surfaces follow the inner surfaces of the ampoule (3030) in a corresponding manner. In this way, a consistent or uniform gap may be formed between the outer surfaces of the insert (3030$i$) and the inner surfaces of the ampoule (3030) even between the conical portions of both, as illustrated.

This gap (3033$i$) creates an annular capillary passage that draws fluid from the ampoule (3030) to the aperture (3037). Insert (3030$i$) may include one or more openings (3034$i$) around its circumference which allows fluid to flow from the center of the ampoule (3030) through the openings (3034$i$) to the annular capillary gap (3033$i$) and to the aperture (3037). The internal surfaces of the annular capillary gap (3033$i$) may be treated with a hydrophilic coating such as HYDROPHILIC COATING FORMULA B (Coating 2Go, Carlisle, MA).

Hence, because the fluid is drawn directly to the aperture (3037) via capillary action through the gap (3033$i$), there is no need for any pumping mechanism. Rather, the capillary action ensures that the movement of fluid to the aperture is independent of the orientation that the ampoule (3030) is held by the user and is further independent of the fluid level contained within the ampoule (3030), i.e., dispensing of the fluid from the ampoule (3030) is independent of gravity. Conventional fluid reservoirs typically require some active pumping mechanism to draw a fluid for dispensing particularly when the fluid level drops relative to the aperture such as when a user holds the fluid reservoir at an extreme angle or when the fluid runs low.

Regardless of the orientation of the ampoule (3030) or the amount of fluid remaining within the ampoule (3030), e.g., when the fluid runs low, the capillary action created between the ampoule (3030) and insert (3033i) ensures that the fluid is drawn to the aperture (3037).

The ampoule (3030) and insert (3030i) can be made of a thermo-plastic polymer such as polypropylene or polyethylene and preferably hydrophilic polymer or a polymer which has its surfaces modified to have hydrophilic properties. Insert (3030i) can be made from hydrophilic porous polypropylene (Porex Corporation, Fairburn, GA). The ampoule may be further provided with a venting hole (3038) which allows for equalization of the pressure as fluid is dispensed from the ampoule. As illustrated, the ampoule (3030) may be provided with a cup or cap (3040) which closes the opening of the aperture (3033) when the device is not in use. The cup or cap (3040) may be attached to the ampoule body by, e.g., thread engagement (3036) (3041) or other engagement mechanism, and seal the tapered end (3032) of the ampoule against tapered hole (3042) in the cup or cap (3040).

When the cup or cap (3040) is fully engaged with ampoule (3030), the aperture (3033) and venting hole (3038) are both sealed. The diameter of venting hole (3038) may range from, e.g., 0.1 to 0.6 mm, which is sufficiently small to prevent outflow or spillage of fluid from the ampoule. The angular dimension (Ang) of conical section (3036) may range from, e.g., 30 to 60 degrees, while the wall thickness (Thk) of the ampoule may range from, e.g., 0.3 to 1 mm. The diameter (D) of the ampoule is generally between, e.g., 4 to 10 mm, while its length (L) may vary based on the desired liquid volume to be stored in the ampoule, liquid volume is generally between, e.g., 0.5 to 3 mL. The ampoule assembly (3000) may further include an end cup (3030c) which seals the ampoule following aseptic drug filling.

Figure 13:
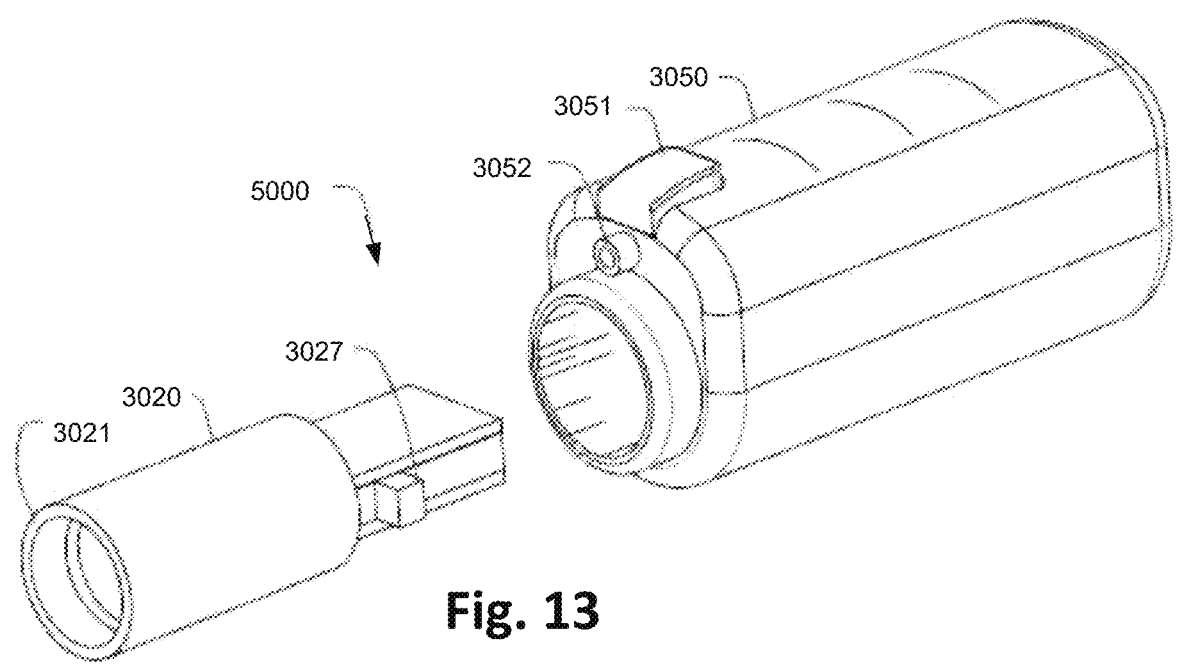

Referring now to FIG. 13 which illustrates an exploded view of fluid ejection device (5000) which includes an ultrasonic transducer (3020) and a housing (3050). Housing (3050) provides an enclosure for the ultrasonic transducer and its electronic circuitry, batteries and further for an optical aiming device (3052). The ultrasonic transducer (3020) may be provided with extensions or protrusions (3027) which capture the ultrasonic dispenser inside the housing (3050). The housing (3050) may be configured into any number of shapes or sizes suitable for holding, manipulation, or carrying by a subject. For instance, the housing (3050) may be generally configured resemble the form factor of a conventional squeeze-bottle eye-dropper to make the device rather intuitive for use by a subject. The housing (3050) may further include an activation switch (3051) and an aiming feature (3052).

Figure 14:
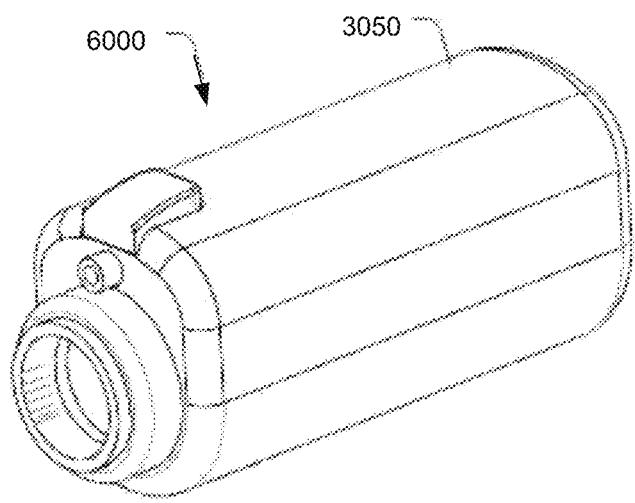
Figure 15:
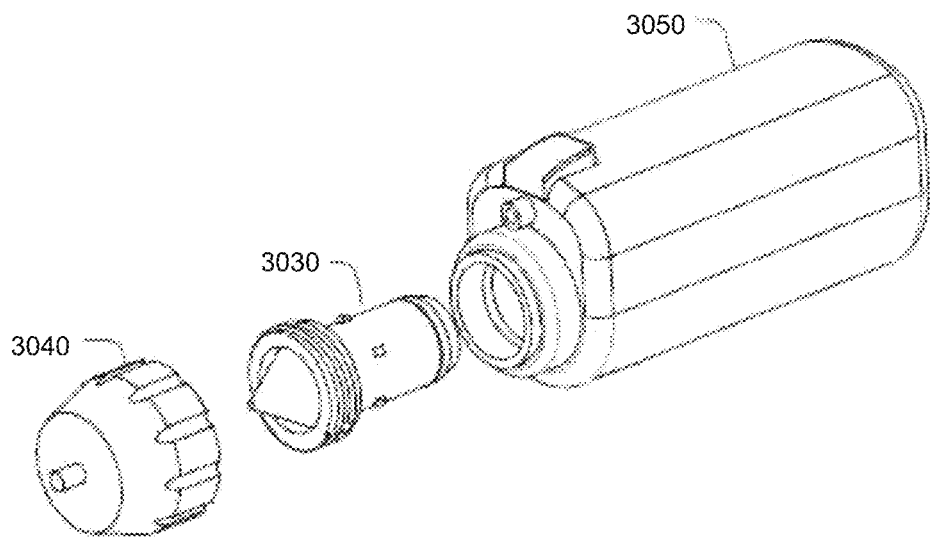
Figure 16:
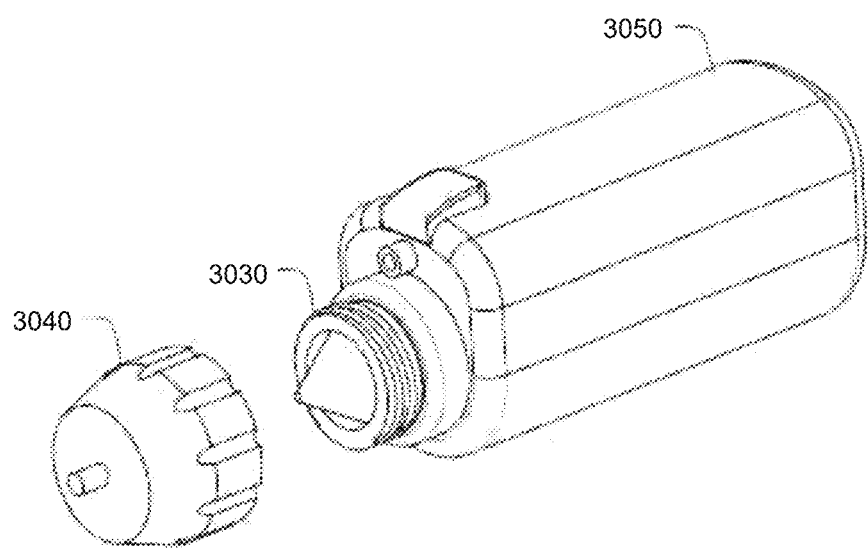

FIG. 14 illustrates the assembly (6000) with the housing (3050) assembled with the ampoule holder (3020) inserted within and FIG. 15 further illustrates the housing (3050) with the ampoule holder (3020) as well as ampoule (3030) in an exploded view showing with the addition of the cup or cap (3040) separately. FIG. 16 illustrates a perspective view of the fluid ejection device showing the housing (3050) when ampoule (3030) is fully inserted into the ampoule holder (3020).

In some embodiments, the fluid ejection device may include an optical apparatus to align or target the dispensing aperture to the ocular surface or to the area of the lower conjunctiva prior to actuation, as further described herein.

Figure 17:
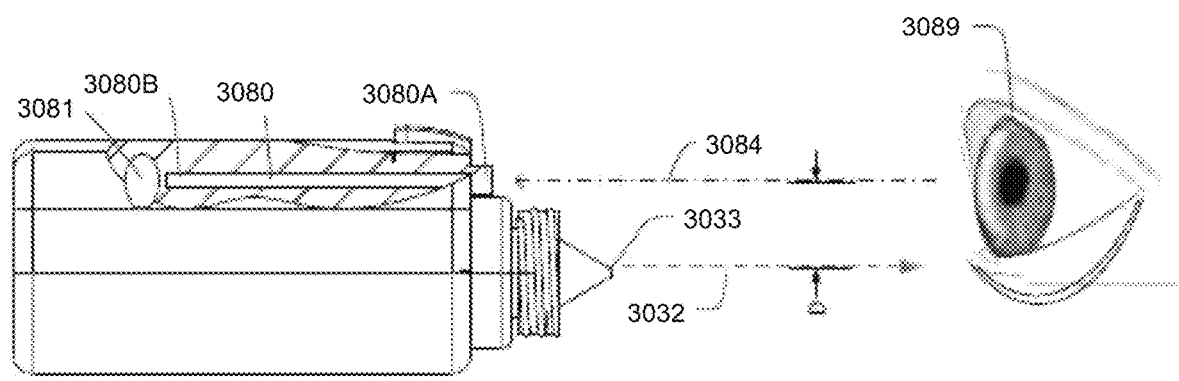

Such alignment assures that the entire dose reaches the surface of the eye. Referring now to FIG. 17, the dispensing device is shown in a partial cross-sectional view with the alignment fixture. In one variation, it can be seen the alignment feature comprises a tubular member (3080) and a light source (3081). The tube (3080) has a proximal opening (3080A) and a distal opening (3080B) while the distal opening is positioned near light source (3081) such as an LED (3081), e.g., red LED, or the like and the proximal opening of the tube (3080A) is brought into proximity near the eye (3089) of the user. The tubular member (3080) is parallel to the droplet projection direction of the droplets (3032) but may be placed in a predetermined offset (D). Prior to actuation of the dispensing device, the user may align the eye to be treated with the proximal opening (3080A) of the tube and then manipulate the orientation of the device until the LED light (3081) at the distal end of the tube becomes visible. In this way the device is brought to an alignment with the optical axis of the eye to be treated or the center of the pupil.

The dispensing nozzle (3033) may be positioned at a predetermined small offset (D) relative to the optical axis of the tube (3084), e.g., 4 to 12 mm, depending on the preset offset (D). When the device is actuated, a stream of fluid (e.g., a continuous stream or discontinuous stream of droplets) will reach the targeted surface of the eye or the conjunctival tissue and deposit fluid at the above mentioned offset from the pupil.

The optical tube (3080) may have a length of, e.g., 20, 30, or 40 mm, while its internal diameter ranges between, e.g., 1 to 5 mm. The internal surfaces of the tube may be optionally coated with optically-black non-reflective coating.

The applications of the disclosed invention discussed above are not limited to the embodiments described, but may include any number of other applications and uses. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A dispensing apparatus, comprising:
an actuator, and
an ampoule containing a liquid to be dispensed, the ampoule including a reservoir portion within which the fluid is contained, a neck portion extending from the reservoir portion, and a fluid path extending between the reservoir portion and neck portion to permit fluid from the reservoir to be directed to the neck portion;
wherein the neck portion includes at least one aperture through a side wall of the neck portion;
wherein the actuator engages with the neck portion via clamping, and wherein a clamping direction of the actuator is substantially perpendicular to a direction of fluid emission from the at least one aperture;
wherein the actuator is configured such that an oscillation of the actuator produces a corresponding oscillation of the neck portion in the direction of fluid emission from the at least one aperture, thereby emitting the liquid to be dispensed from the at least one aperture in a direction substantially perpendicular to the fluid path.

2. The apparatus of claim 1 wherein the neck portion has a cross-sectional shape selected from the group consisting of: circular, oval, triangular, square, pentagonal, hexagonal and octagonal.

3. The apparatus of claim 1 wherein the neck portion is secured to the actuator via an interference fit.

4. The apparatus of claim 1 wherein an operating frequency of the apparatus is near or at a resonance frequency of the actuator.

5. The apparatus of claim 1 wherein a clamping force of the actuator upon the neck portion is less than 5 N.

6. The apparatus of claim 1 wherein the actuator comprises a bending transducer configured to oscillate in a bending mode.

7. The apparatus of claim 6 wherein the bending transducer comprises a bimorph actuator having a first piezoceramic layer, a second piezoceramic layer, and a passive layer between the first and second piezoceramic layers.

8. The apparatus of claim 7 wherein the passive layer comprises a printed circuit board.

9. The apparatus of claim 6 wherein the bending transducer comprises a unimorph actuator having a piezoceramic layer.

10. The apparatus of claim 6 further comprising electronic circuitry programmed to drive the actuator.

11. The apparatus of claim 1 wherein an oscillation amplitude of the actuator is less than 2 micron.

12. The apparatus of claim 1 wherein the fluid comprises ophthalmic medication.

13. The apparatus of claim 1 further comprising an optical alignment system which enables a patient to align the at least one aperture to a targeted region on a surface of an eye of the patient.

14. The apparatus of claim 1, wherein the direction of fluid emission is substantially horizontal.

15. The apparatus of claim 1, wherein the fluid to be dispensed passes through a gap in the actuator as the fluid is dispensed through the aperture.

16. The apparatus of claim 1, wherein the direction of fluid emission is substantially normal to a longitudinal axis of the neck portion.

17. The apparatus of claim 14, wherein the direction of fluid emission is coplanar with a portion of the clamping direction.

\* \* \* \* \*